(12) United States Patent
McManus et al.

(10) Patent No.: US 8,574,300 B2
(45) Date of Patent: Nov. 5, 2013

(54) EXPANDABLE INTERBODY SPACER DEVICE

(75) Inventors: Joshua McManus, Downingtown, PA (US); William Woodburn, Mantua, NJ (US); Walter Widmer, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 405 days.

(21) Appl. No.: 12/921,242

(22) PCT Filed: Mar. 5, 2009

(86) PCT No.: PCT/US2009/036148
§ 371 (c)(1),
(2), (4) Date: Sep. 7, 2010

(87) PCT Pub. No.: WO2009/114381
PCT Pub. Date: Sep. 17, 2009

(65) Prior Publication Data
US 2011/0015747 A1    Jan. 20, 2011

(51) Int. Cl.
*A61F 2/44* (2006.01)
(52) U.S. Cl.
USPC ................ 623/17.16; 623/17.11; 623/17.15
(58) Field of Classification Search
USPC ............... 623/17.11, 17.13, 17.15, 17.16; 606/105, 246–249, 90; 600/207
See application file for complete search history.

(56) References Cited

U.S. PATENT DOCUMENTS

| | | | |
|---|---|---|---|
| 4,863,476 A | 9/1989 | Shepperd | |
| 5,397,364 A | 3/1995 | Kozak et al. | |
| 5,522,899 A | 6/1996 | Michelson | |
| 5,609,635 A | 3/1997 | Michelson | |
| 5,658,335 A | 8/1997 | Allen | |
| 5,665,122 A | 9/1997 | Kambin | |
| 5,782,919 A | 7/1998 | Zdeblick et al. | |
| 5,800,547 A | 9/1998 | Schafer et al. | |
| 5,865,848 A | 2/1999 | Baker | |
| 6,045,579 A | 4/2000 | Hochshuler et al. | |
| 6,080,193 A | 6/2000 | Hochshuler et al. | |
| 6,102,950 A | 8/2000 | Vaccaro | |
| 6,176,881 B1 * | 1/2001 | Schar et al. | 623/17.11 |
| 6,176,882 B1 | 1/2001 | Biedermann et al. | |

(Continued)

FOREIGN PATENT DOCUMENTS

| | | |
|---|---|---|
| DE | 9407806 U1 | 7/1994 |
| DE | 4416605 C1 | 6/1995 |

(Continued)

OTHER PUBLICATIONS

Notification of Transmittal of the International Preliminary Report on Patentability dated Jun. 6, 2014 for corresponding International Application No. PCT/US2009/036148.

*Primary Examiner* — Todd Manahan
*Assistant Examiner* — Jessica Weiss
(74) *Attorney, Agent, or Firm* — Stradley Ronon Stevens & Young, LLP

(57) ABSTRACT

An expandable interbody spacer (10) is provided that includes a pair of oppositely facing endplate components (20, 40) and an interior component that includes one or more vertically extending stacks of arranged C-clip members (70) radially surrounding one or more bosses (30) protruding interiorly from one of the endplates, wherein the size and configuration of the bosses and the c-clip members are designed to allow the incremental expansion of expandable interbody spacer.

21 Claims, 18 Drawing Sheets

(56) References Cited

U.S. PATENT DOCUMENTS

| | | |
|---|---|---|
| 6,251,140 B1 | 6/2001 | Marino et al. |
| 6,290,724 B1 | 9/2001 | Marino |
| 6,368,325 B1 | 4/2002 | McKinley et al. |
| 6,375,683 B1 | 4/2002 | Crozet et al. |
| 6,419,705 B1 | 7/2002 | Erickson |
| 6,443,990 B1 | 9/2002 | Aebi et al. |
| 6,447,547 B1 | 9/2002 | Michelson |
| 6,454,806 B1 | 9/2002 | Cohen et al. |
| 6,500,205 B1 | 12/2002 | Michelson |
| 6,562,074 B2 | 5/2003 | Gerbec et al. |
| 6,641,614 B1 | 11/2003 | Wagner et al. |
| 6,648,917 B2 | 11/2003 | Gerbec et al. |
| 6,652,584 B2 | 11/2003 | Michelson |
| 6,706,070 B1 | 3/2004 | Wagner et al. |
| 6,709,458 B2 | 3/2004 | Michelson |
| 6,716,247 B2 | 4/2004 | Michelson |
| 6,719,796 B2 | 4/2004 | Cohen et al. |
| 6,723,126 B1 | 4/2004 | Berry |
| 6,733,535 B2 | 5/2004 | Michelson |
| 6,793,679 B2 | 9/2004 | Michelson |
| 6,814,756 B1 | 11/2004 | Michelson |
| 6,830,589 B2 | 12/2004 | Erickson |
| 6,852,129 B2 | 2/2005 | Gerbec et al. |
| 6,863,673 B2 | 3/2005 | Gerbec et al. |
| 6,902,579 B2 | 6/2005 | Harms et al. |
| 6,953,477 B2 | 10/2005 | Berry |
| 6,962,606 B2 | 11/2005 | Michelson |
| 6,972,035 B2 | 12/2005 | Michelson |
| 6,997,929 B2 | 2/2006 | Manzi et al. |
| 7,008,453 B1 | 3/2006 | Michelson |
| 7,018,415 B1 | 3/2006 | McKay |
| 7,029,498 B2 | 4/2006 | Boehm et al. |
| 7,066,961 B2 | 6/2006 | Michelson |
| 7,118,598 B2 | 10/2006 | Michelson |
| 7,156,874 B2 | 1/2007 | Paponneau |
| 7,211,112 B2 | 5/2007 | Baynham et al. |
| 7,282,063 B2 | 10/2007 | Cohen et al. |
| 7,311,713 B2 | 12/2007 | Johnson et al. |
| 2005/0038512 A1 | 2/2005 | Michelson |
| 2005/0049590 A1 | 3/2005 | Alleyne et al. |
| 2005/0125062 A1 | 6/2005 | Biedermann et al. |
| 2005/0171552 A1 | 8/2005 | Johnson et al. |
| 2005/0209698 A1 | 9/2005 | Gordon et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0058807 A1 | 3/2006 | Landry et al. |
| 2006/0058876 A1 | 3/2006 | McKinley |
| 2006/0058880 A1* | 3/2006 | Wysocki et al. ........... 623/17.15 |
| 2006/0069436 A1 | 3/2006 | Sutton et al. |
| 2006/0122701 A1 | 6/2006 | Kiester |
| 2006/0149385 A1 | 7/2006 | McKay |
| 2006/0229729 A1* | 10/2006 | Gordon et al. ............. 623/17.16 |
| 2006/0253201 A1 | 11/2006 | McLuen |
| 2007/0239279 A1 | 10/2007 | Francis |
| 2008/0161933 A1* | 7/2008 | Grotz et al. ................ 623/17.16 |
| 2009/0192617 A1* | 7/2009 | Arramon et al. ........... 623/17.16 |

FOREIGN PATENT DOCUMENTS

| | | |
|---|---|---|
| DE | 20104863 U1 | 5/2001 |
| FR | 27341448 A1 | 11/1996 |
| FR | 2874814 A | 3/2006 |
| WO | WO 9700054 | 1/1997 |

* cited by examiner

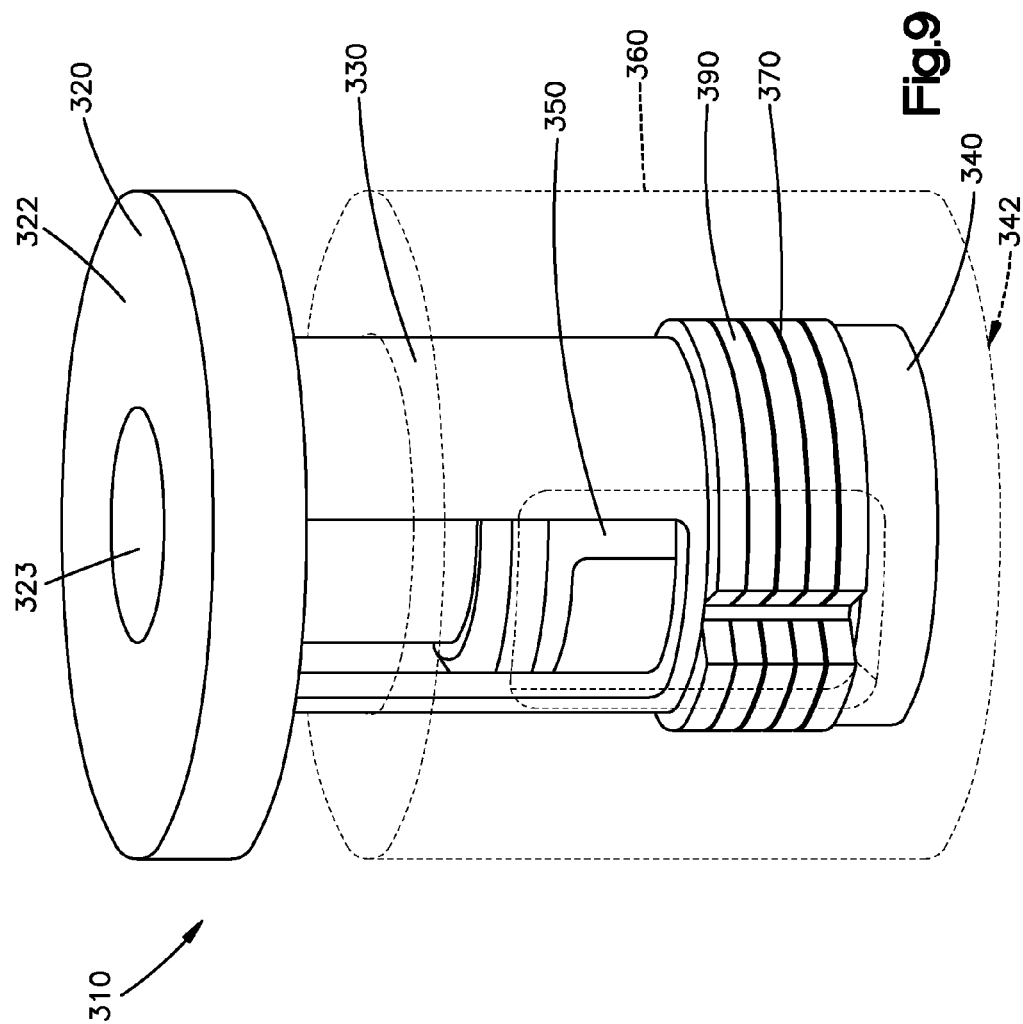

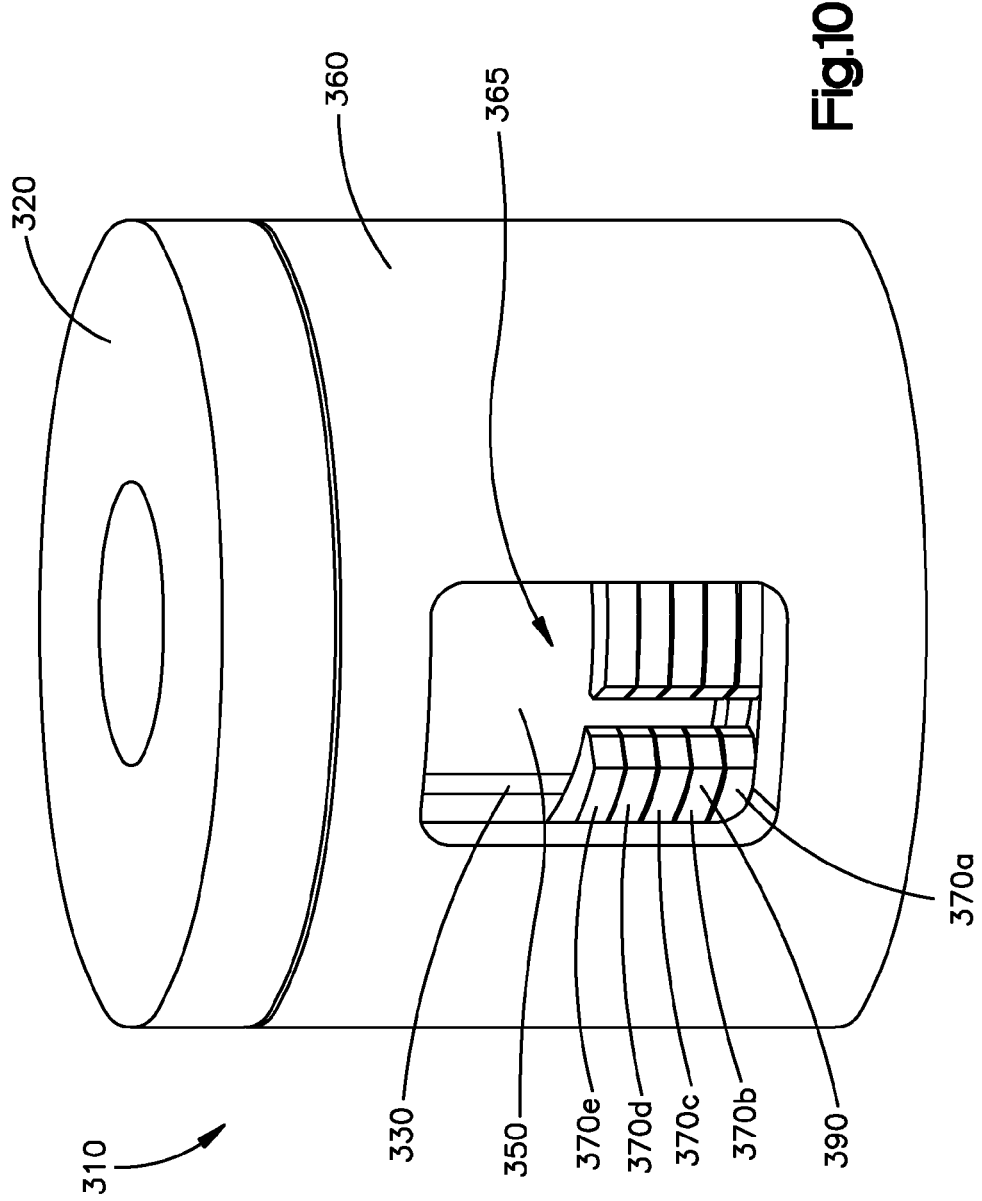

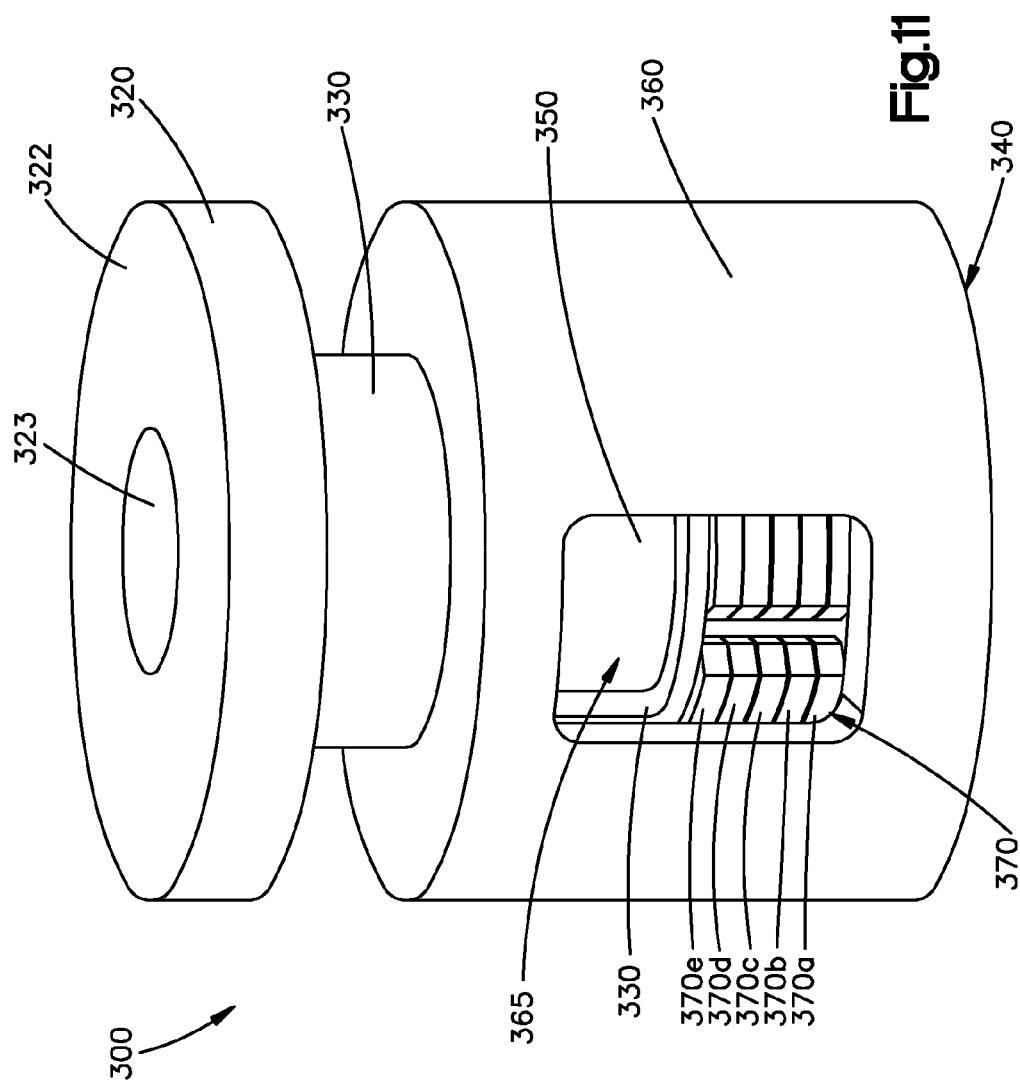

EXPANDABLE INTERBODY SPACER DEVICE

CROSS-REFERENCE TO RELATED APPLICATIONS

This application claims the benefit of U.S. Provisional Application No. 61/034,713, filed on Mar. 7, 2008, entitled "EXPANDABLE INTERBODY SPACER DEVICE," the contents of which is incorporated in its entirety by reference herein.

BACKGROUND OF THE INVENTION

Interbody fusion spacers are utilized to restore physiological space between two adjacent vertebrae and to maintain the space while fusion occurs between the adjacent vertebrae. The surgeries used to place such spacers can be painful for the patient and the size of the incision and approach channel provides challenges. It is desirable to develop an interbody spacer that promotes fusion while minimizing the size of the incision required for implantation of the spacer. An interbody spacer that assumes a collapsed configuration and subsequently deploys into an expanded configuration within the disc space may enable fusion while reducing the size of the required surgical incision. The surgical procedure utilized with such a spacer may also permit a surgeon to distract and size the disc space with the spacer itself as opposed to using multiple separate instruments for distraction. It would be advantageous to insert a relatively small spacer through a relatively small opening and expand the spacer to fit the disc space, or disc and vertebral space, appropriately. In this manner the surgical incision may be relatively small while the anterior column height of the spine can be restored.

BRIEF SUMMARY OF THE INVENTION

In accordance with one aspect of the present invention an expandable interbody implant, spacer or corpectomy device (interchangeably referred to as a spacer, implant or corpectomy device) for implantation between vertebra has a collapsed condition and an expanded condition. The spacer may comprise a superior or top component having an external surface for contacting at least a portion of one vertebrae, and an inferior or bottom component having an external surface for contacting at least a portion of another vertebrae. The superior and inferior components preferably are moveable relative to each other so that the spacer may move between the collapsed condition and the expanded condition. Preferably at least one boss member is positioned between and moveable relative to at least one of the superior component and interior component. The boss member may include a side surface and a distal end surface. One or more expandable clip members are preferably stacked one on top of the other to form at least one stack of clips, wherein each clip member preferably has a top surface, a relaxed position, a deflected position, and defines a space.

Preferably, the boss member passes through the space in the clip member when the clip member is in the deflected position and the clip member preferably interferes with the movement of and does not permit the boss member to pass through the space when the clip member is in the relaxed position. Preferably each of the clip members in the stack deflects in a series to the relaxed position as the distal end surface of the boss member passes a top surface of each of the clips as the spacer expands, thereby allowing the spacer to expand in predefined increments.

Preferably all the clip members in the spacer are in the deflected position when the spacer is in the collapsed position. The clip members may have integral, resilient and elastically deflectable arms that move upon application of a force. The clip members may be formed of a single piece of material and integrally connected. The spacer may have more than one stack of clip members, each stack preferably comprising a plurality of clip members.

The superior component of the spacer preferably includes at least one boss member extending toward the inferior component and the inferior component preferably includes at least one post member extending from the inferior component toward the superior component, or vice versa. The post member is preferably associated with the boss member such that the post member may telescope with respect to the boss member as the implant expands and collapses. The spacer may have one or more boss members, one or more post members and one or more stacks of clip members. The boss member(s) may have a recess and the post member(s) may move within the recess as the implant moves between the collapsed and expanded conditions. The clip members may have resilient arms that expand or collapse upon application of a force. The arms of the resilient clip members may be circularly shaped, C-shaped, U-shaped, Y-shaped, or V-shaped, or have other shapes. The clip members may be secured to, connected to, integral with or unconnected to the inferior component.

The plurality of stacks of clip members may be connected by a central member located between the plurality of boss members. The plurality of stacked resilient clips may form one or more separate stacks of resilient clip members, each stack of clip members being associated with a different boss member. The clip members may be substantially flat and relatively uniform in thickness. Alternatively, the clip members may have a non-uniform thickness, such as, for example, a wedge shape, and may alternatively or in addition have a curved surface. The clip members may be shaped or otherwise configured and connected in a manner to provide an angle of lordosis or lordotic curve, or to provide an angle of kyphosis or kyphotic curve. The superior and inferior components include edges along their perimeter and the separately stacked clip members may be located between the boss members and perimeter edges of the superior and inferior components. The boss members and the post members are preferably cylindrically-shaped.

The clip members preferably move to a relaxed position underneath the boss member as the distal end of the boss member passes the top surface of the clip member and supports the superior component when subjected to axial compression. The clip members are preferably configured and arranged so that they are in compression when axial loads are applied to the spacer. It is also possible to load the clips in shear and in bending. The clip members may have arms that are expanded and move away from each other when the clip member is changed to the deflected position such that the space defined by the clip member is larger. Alternatively, the clip members may have arms that deflect inwardly when the clip members are changed to the deflected position and the arms expand to the relaxed position.

In another embodiment, an expandable interbody spacer includes a pair of oppositely facing endplate components and an interior component that includes one or more vertically extending stacks of arranged C-clip members radially surrounding one or more bosses protruding interiorly from one of the endplates. The bosses and the c-clip members preferably are designed to allow incremental expansion of the expandable interbody spacer.

The spacer may further include a stop mechanism to limit the expansion of the spacer. Other features and configurations are contemplated and will be apparent to one having skill in the art.

BRIEF DESCRIPTION OF THE DRAWINGS

The foregoing summary, as well as the following detailed description of preferred embodiments of the application, will be better understood when read in conjunction with the appended drawings. The drawings, examples and embodiments described within this specification are for the purposes of describing and enabling the best mode of the preferred expandable interbody spacer and the preferred method of implanting the expandable interbody spacer of the present invention and are to be understood as illustrative and exemplary of structures, features, aspects and methods of using the present invention and not as limiting the scope of the invention. It should be understood that the application is not limited to the precise arrangements and configurations shown. In the drawings:

FIG. 9 illustrates a front perspective view of a fourth embodiment of an expandable corpectomy device in accordance with the present invention, with portions shown in phantom for clarity;

FIG. 10 illustrates a front perspective view of the expandable corpectomy device shown in FIG. 9 in a collapsed condition;

FIG. 11 illustrates a front perspective view of the expandable corpectomy device shown in FIG. 10 in a partially expanded condition;

DETAILED DESCRIPTION OF THE INVENTION

Figure 1:
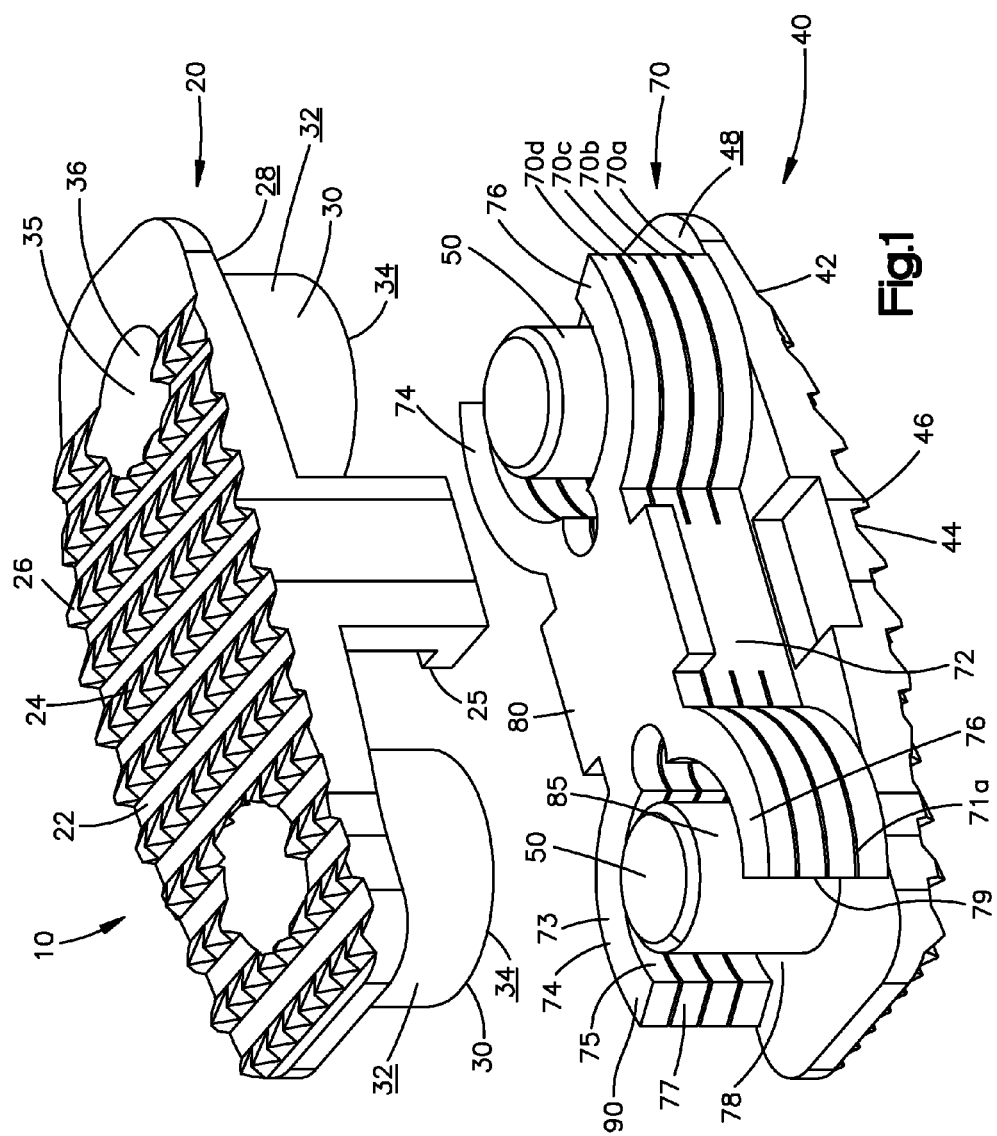
FIG. 1 illustrates a top perspective, partially exploded view of an expandable interbody spacer, implant, or corpectomy device in accordance with a first embodiment of the present invention.

The embodiments, implants, systems, kits, methods and examples described within this specification are to be understood as illustrative and exemplary of the structures, features and aspects of the implant, system, kit and method of the present invention and not as limiting the scope of the invention. The features, structures, aspects and steps of the implant, system and method may be used singularly, alternatively or together as desired or appropriate. Certain terminology is used in the following description for convenience only and is not to be used in a limiting manner or to be limiting in nature. The words "right", "left", "lower" and "upper" designate directions in the drawings to which reference is made. The words "inwardly" and "outwardly" refer to directions toward and away from, respectively, the geometric center of the interbody spacer, the implant, the corpectomy device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import. While the expandable spacer embodiments may be described as being placed in the spine, and more specifically as being placed in a spinal disc space between vertebrae, or as a replacement for both vertebra and spinal discs, as may be appropriate and desired, the spacer may have additional application in areas other than the spine, such as, for example, long bones, other bones, soft tissue and as a spacer in non-medical applications.

Figure 2:
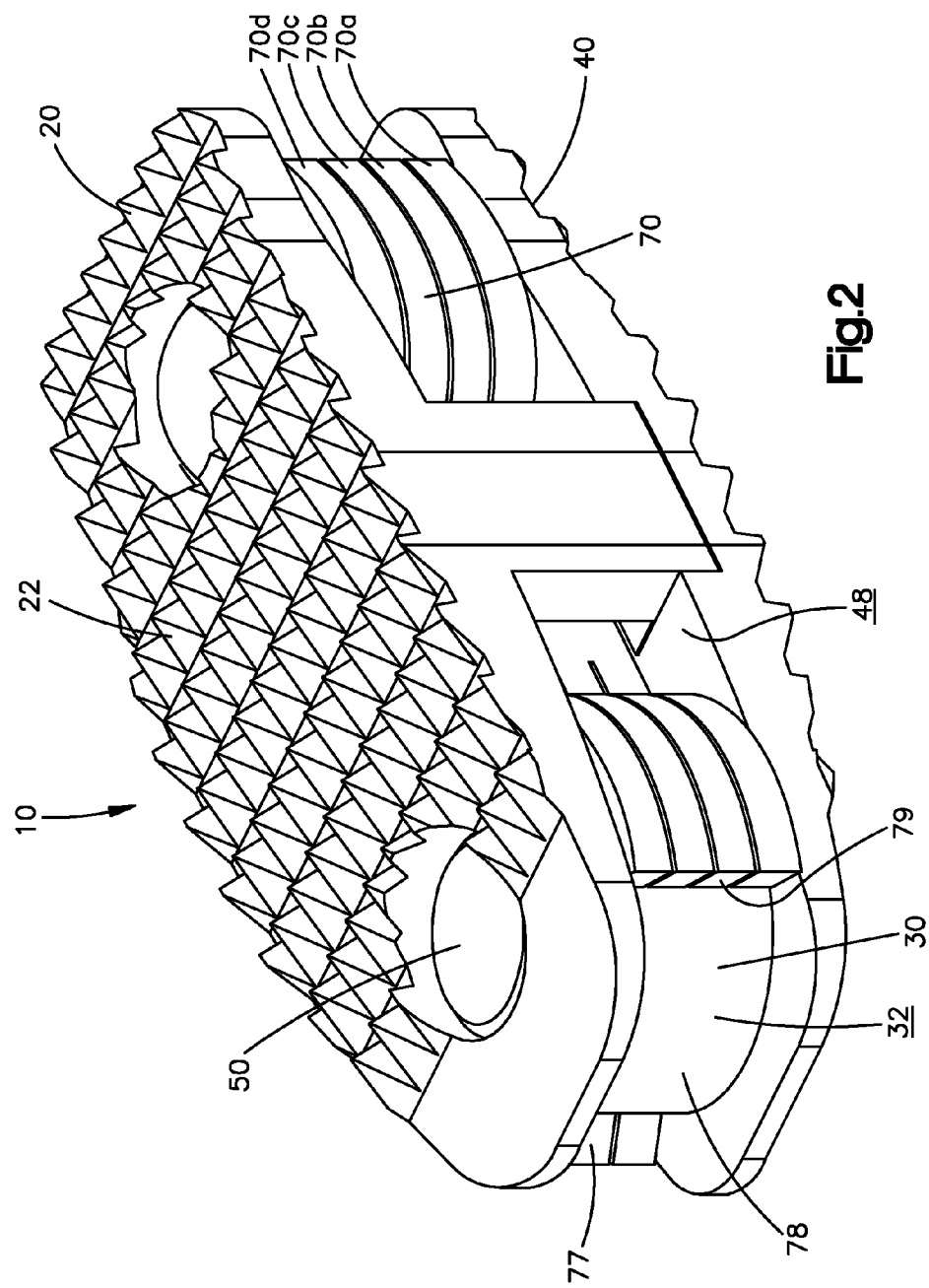
FIG. 2 illustrates a top perspective view of the expandable interbody spacer of FIG. 1 in a collapsed configuration.
Figure 3:
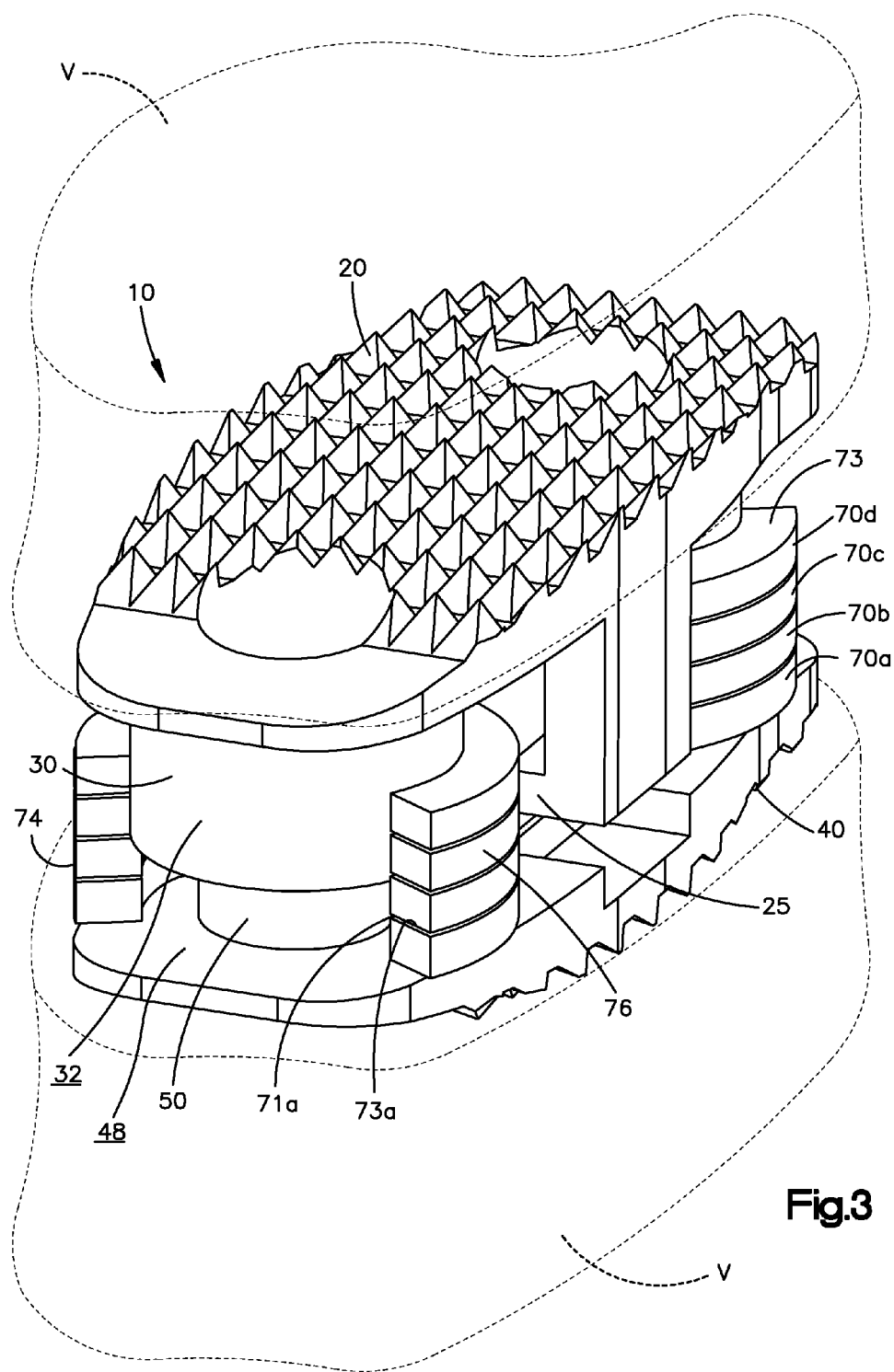
FIG. 3 illustrates a top perspective view of the expandable interbody spacer of FIG. 1 in a partially expanded configuration.

Referring to FIGS. 1-3, a first embodiment of an expandable interbody spacer 10 includes a superior component 20 and an inferior component 40, each of which includes an endplate 22, 42 that provides a contact surface 24, 44 for engaging adjacent vertebra V in an implanted position. The expandable interbody spacer 10 is preferably mounted between the adjacent vertebrae V and expanded to restore disc height at a damaged disc segment. In the first embodiment, the endplates 22, 42 of the superior component 20 and the inferior component 40 may include a series of teeth, ridges, spikes, keels, and/or surface texturing, generally shown at 26, 46, to increase the coefficient of friction between the endplates 22, 42 of the expandable interbody spacer 10 and the adjacent vertebrae V, or to otherwise provide a mechanism for the endplates 22, 42 to engage the vertebrae V, thereby resisting movement of the interbody spacer 10 when inserted between adjacent vertebrae V. Further, the endplates 22, 42 may include a surface texturing or coating to assist or promote bony in-growth or on-growth between the vertebral endplates and the implant endplates 22, 42 to further secure the spacer 10 in position.

The superior component 20 of the first embodiment include two boss members 30, but is not so limited and may include a single or more than two boss members 30, protruding from an inferior surface 28 toward the inferior component 40 in an assembled configuration. The boss members 30 include a side surface 32 and a distal end surface 34. The inferior component 40 preferably includes two post members 50, but is also not so limited and may include a single or more than two post members 50, extending from a superior surface 48 toward the superior component 20 in the assembled configuration. Each of the post members 50 are operatively associated with the bosses 30 so that the boss members 30 are axially translatable relative to the post members 50 in the assembled configuration. The bosses 30 and the post members 50 are not limited to being arranged in the described and illustrated manner and may be arranged in an opposite manner or may be otherwise constructed to permit generally linear or axial movement of the superior component 20 toward and/or away from the inferior component 40. In addition, the boss members 30 and post members 50 may be arranged in a manner to permit angular or rotational movement of the superior and inferior components 20, 40 relative to each other such that the components 20, 40 may be moved toward and away from each other at the direction of a surgeon or user.

The expandable interbody spacer 10 of the first embodiment further includes one or more clips 70. The clips 70 are preferably stacked one atop the other between the superior and inferior components 20, 40 in the assembled configuration. The clips 70 are preferably constructed of a resilient material and include resilient arms 74, 76 that are flexible and define a space 75 therebetween. The resilient arms 74, 76 also define an opening 78 between the distal ends 77, 79. The arms 74, 76 may elastically flex or move so that the space 75 and opening 77 can be enlarged or decreased. The stacked clips 70 may be integrally formed such that at least a connecting portion 72 continuously joins the entirety of the stacked clips 70 and the clips 70 may be fabricated from the same piece of material. The stacked clips 70 may alternatively be fabricated from several pieces of material or may be independently formed and disposed or secured one on top of the other. The stacked clips 70 of the first embodiment are comprised of individual clip members 70a, 70b, 70c, 70d independently stacked between the post members 50. Each clip member 70a, 70b, 70c, 70d preferably has a non-deflected state (FIG. 1), also referred to as a relaxed position, in which the space 75 of each clip member 70a, 70b, 70c, 70d is a first size that is different than when the clip members 70a, 70b, 70c, 70d are moved to the deflected state (FIG. 2), also referred to as a deflected position. In the first embodiment, the clips 70 in the deflected state are expanded so that the space 75 is larger in comparison to the size of the space in the relaxed position. The clips may be expanded through interaction with the side surfaces 32 of the boss members 30. Alternatively, the clips 70 could be deflected inwardly such that the space 75 is smaller in the deflected state in comparison to the size of the space 75 in the relaxed position.

The stacked clips 70 are preferably disposed or secured to the inferior component 40 such that the clip members 70a, 70b, 70c, 70d are proximate both the bosses 30 and the post members 50 in the assembled configuration (FIGS. 2 & 3). The stacked clips 70 may alternatively be unconnected to either the superior or inferior component 20, 40. When the expandable interbody spacer 10 is in a fully collapsed state (FIG. 2), the bosses 70 are disposed interior to and in the space 75 of the clip members 70a, 70b, 70c, 70d, and the clips 70 assume their deflected or expanded state due to being deflected outward by the bosses 30. An instrument (not shown), such as a spreader instrument, can be used to move the superior component 20 relative to the inferior component 40, by grasping and urging the superior and inferior components 20, 40 away from each other. As the superior component 20 is moved away from the inferior component 40, the clip members 70a, 70b, 70c, 70d sequentially deflect inwardly as the distal end surface 34 passes upper surfaces of each individual clip member 70a, 70b, 70c, 70d to a position underneath the bosses 30. Depending upon the number of individual clip members 70a, 70b, 70c, 70d, the expandable spacer 10 may be positioned in a range of incrementally expanded sizes to distract a collapsed disc-space and restore height thereto. Physiological load is borne by the expandable interbody spacer 10 as it experiences axial compression through the bottom facing or end surfaces 34 of the bosses 30 onto the topmost deflected clip members 70a, 70b, 70c, 70d or directly onto the inferior component 40, depending upon wherein the distal end surface 34 is positioned.

The boss members 30 of the first embodiment are cylindrically-shaped and hollow. Each of the boss members 30 include a recess or cavity 35 formed therein with an opening 33 to accept the post members 50 and an opening 36 exposed at the superior endplate 22.

The post members 50 of the first embodiment are cylindrically-shaped and may be hollow or solid. The outside diameter of the post members 50 are preferably slightly smaller than the diameter of the cavity 35 in the boss members 30 so that the post members 50 are slidably received within the boss members 30. Accordingly, the boss members 30 are axially translatable up and down relative to the cylindrical post members 50. As the implant 10 expands in height, the superior component 20 moves away from the inferior component 40 and the boss members 30 move relative to the post members 50.

In the first embodiment, the stacked resilient clips 70 are comprised of a pair of oppositely-facing C-shaped clips 70 joined together by a connecting portion 72. The clips 70 are preferably secured to the anterior component 40 and each clip member 70a, 70b, 70c, 70d surrounds at least a portion of one of the post members 50. More specifically, the post members 50 extend between the arms 74, 76 of the clip 70 and through the space 75. The resilient C-clips 70 may be formed integrally with the anterior component 40 and a gap or space 85 is preferably left between the exterior surface of the post member 50 and the interior surface of the resilient clip arms 74, 76.

Specifically, in the first embodiment, the stacked C-clips 70 are comprised of four C-clips 70a, 70b, 70c, 70d stacked on the inferior component 14. With the implant in the collapsed position as shown in FIG. 2, the boss members 30 slide down over the post members 50. The outside diameter, shape, size and/or configuration of the boss members 30 is slightly larger than the space 75 when the clip members are in the relaxed position such that in order to permit the boss member to slide down over the post members, the arms of each pair of the four resilient clips 70a, 70b, 70c & 70d are expanded to the expanded state (deflected state) or expanded position (deflected position) where the arms 74, 76 permit the boss members 30 to pass through. The implant preferably is placed in the desired position in bone while in the completely collapsed position. With the implant in position, a distractor preferably is used to expand the implant. In use, the distractor moves the superior component 20 away from the inferior component 40, which in turn moves the boss members 30 relative to the post members 50. As the boss member 30 moves past the top edge 71a of the first clip 70a, the resilient arms 74a, 76a are no longer held in the expanded position and move to the relaxed position where the top surface 73a of the resilient clip 70a is positioned underneath the distal end surface 34 of the boss member 30. If expansion of the implant continues, the boss member 30 continues to move relative to the post member 50 until the distal end 34 of the boss member moves past the top edge 71b of the second clip 70b whereupon the resilient arms 74b, 76b move to the relaxed position where the top surface 73b of the resilient clip 70b is positioned underneath the distal end surface 34 of the boss member 30 as shown in FIG. 3. In FIG. 3, the stacked C-clips 70 are arranged such that the third and fourth clips 70c, 70d remain in the expanded state pressing against external side surfaces 32 of the bosses 30, while the first and second clips 70a, 70b are in the non-expanded state, or relaxed position, generally blocking or preventing the bosses 30 and the superior component 20 from moving toward the inferior component 40, thereby maintaining at least the illustrated distance between the contact surfaces 22, 42 and any adjacent vertebrae that the expandable interbody spacer 10 is positioned between.

The expandable implant 10 will maintain its height because any compressive force exerted on the end plates 22, 42 is transmitted to the boss members 30, which transmits such forces to the resilient clips 70 located beneath the bosses 30, which transmits the force to the inferior component 40. Preferably the clip members and implant design are configured and arranged so that the clip members are in pure compression when axial loads are applied to the implant. Alternatively or additionally, the clip members may be loaded in shear, bending or both.

While the embodiment of FIGS. 1-3 show four stacked, resilient clips it will be appreciated that more or less resilient clips may be included to permit more or less of a height differential between the fully expanded and fully collapsed position. For example, the implant may only utilize one clip, or a plurality of clips as shown in FIGS. 1-3. The clip members may be relatively flat and relatively uniform in thickness. Alternatively or additionally, the clip members may have a non-uniform thickness, such as, for example, a wedge shape, and may alternatively or additionally have a curved surface. The clip members may be shaped or otherwise configured and connected in a manner to provide an angle of lordosis or lordotic curve, or to provide an angle of kyphosis or kyphotic curve.

The thickness of the resilient clips preferably determines the increments of height adjustment of the implant. For example, if four uniform clips of 2 mm in thickness are utilized, the implant spacer will have a total height adjustment range of 8 mm, in 2 mm increments. The resilient clips all may be the same thickness, different thickness or a mixture of different thickness where some clips have the same thickness and others do not. The resilient clips in the embodiment of FIGS. 1-3 are connected at the central portion of the clips and are positioned in the center of the implant. The clips may be located in other areas of the implant and have different configurations. Moreover, while the clips in FIGS. 1-3 are generally C-shaped and referred to as C-clips, (which are aligned back to back to form a dog-bone shape), the clips may have other shapes such as for example, U-shaped, Y-shaped, V-shaped, circularly shaped or other shapes.

Additionally, as shown in the embodiment of FIGS. 1-3, there may be included one or more protrusions on the superior or inferior component 20, 40 that serve as a mechanical stop to prevent the expandable interbody spacer 10 from expanding too far and disassembling. For example, the superior component 20 in the first embodiment includes a mechanical stop 25 and the top most C-clip 70d of the stacked C-clips 90 includes an overhang 80 that engage each other in a fully extended position to prevent the expandable interbody spacer 20 from expanding too far and disassembling. The interbody spacer 10 is not limited to inclusion of the above-described mechanical stop 25 and overhang 80 and may include alternative mechanisms to prevent disassembly of the spacer 10 during expansion, or may not include such an overextension stop or disassembly mechanism without significantly impacting the operation of the spacer 10.

The stacked C-clips 70 are not limited to being positioned on the inferior component 40 and may be formed integrally with the inferior component 40 such that the inferior component 40 and the stacked C-clips 70 are one component. The stacked C-clips can be unconnected to either the superior or inferior component, or may be connected or secured to the superior component or integral with the superior component. In addition, the bosses 30 can be solid, not hollow, and the stacked C-clips 70 can be formed integral to the inferior component 40 or otherwise secured thereto, and the post members 50 may be unnecessary. While the bosses 30 have been illustrated as hollow with the post members inserted into the hollow cavity, the bosses 30 and post members 50 can be arranged as side by side projections that translate relative to each other and which may or may not be interconnected.

While the embodiment of FIGS. 1-3 has endplates that have a length greater than twice the width and are generally configured for a posterior interbody fusion procedure where an implant is inserted on each side of the spinous process, the principles can be applied to different shapes and configurations of spacers.

Figure 4:
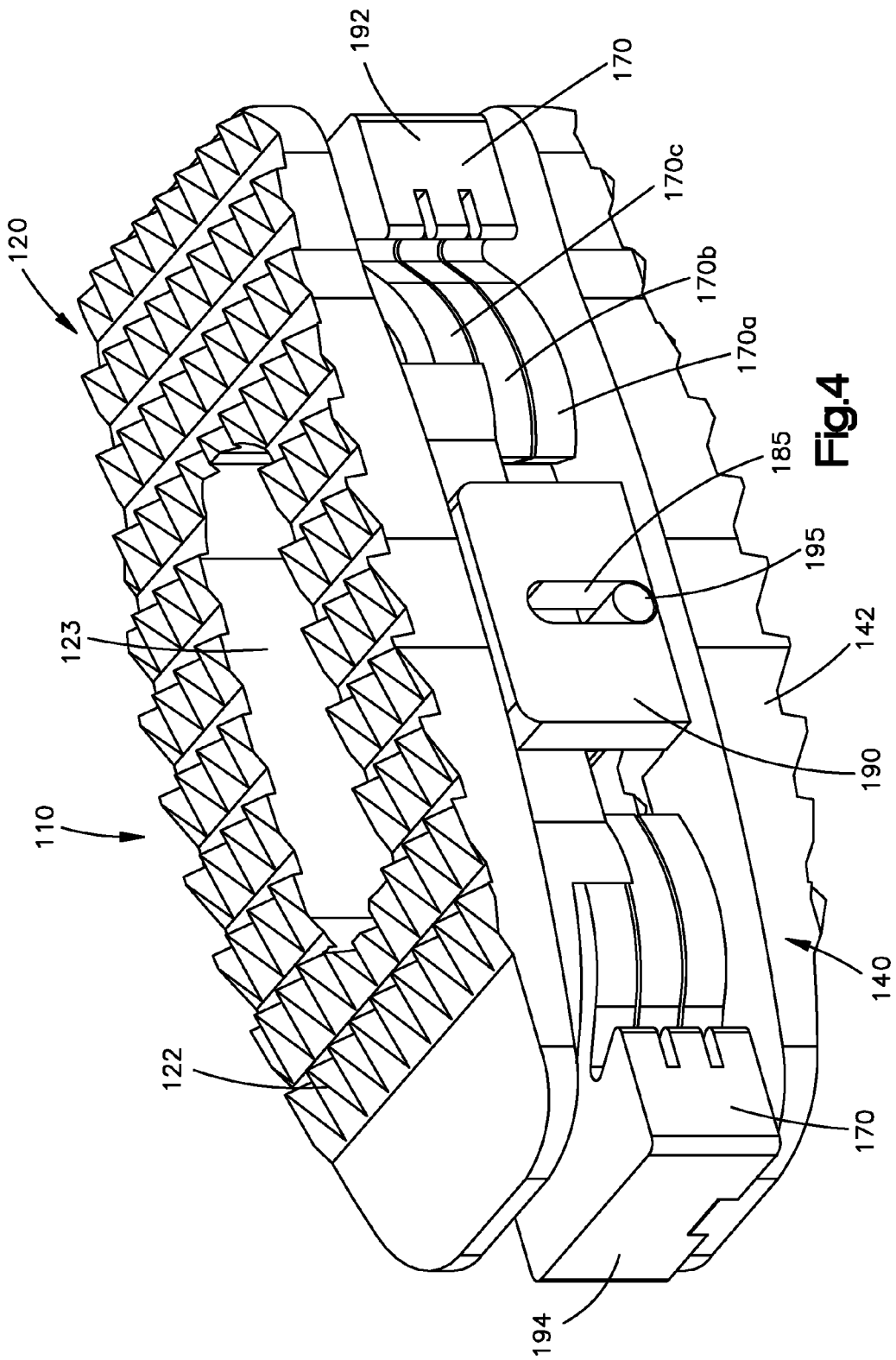
FIG. 4 illustrates a side perspective view of an expandable interbody spacer in accordance with a second embodiment of the present invention.
Figure 5:
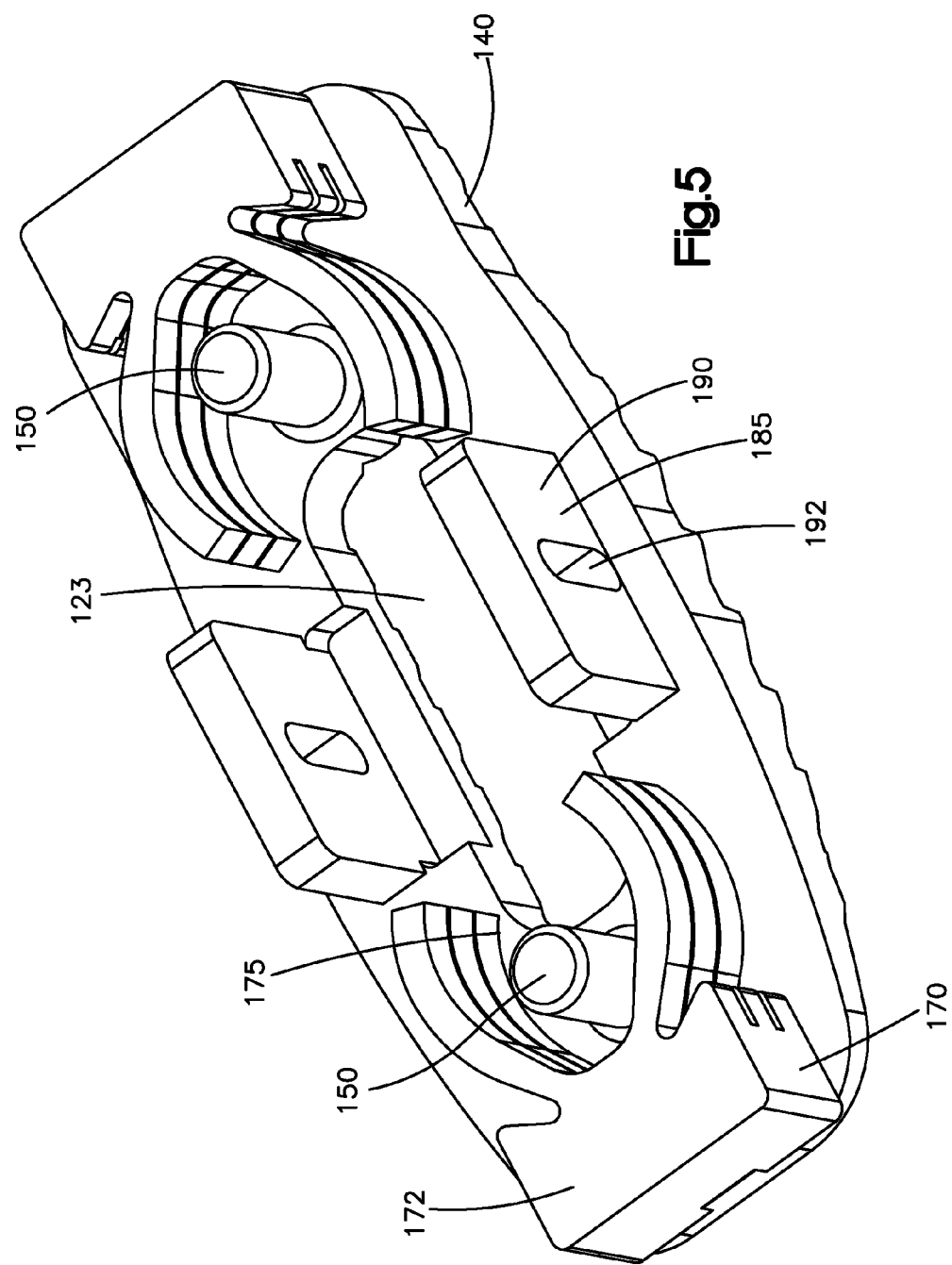
FIG. 5 illustrates a top perspective view of inferior and intermediary components of the expandable interbody spacer shown in FIG. 4.
Figure 6:
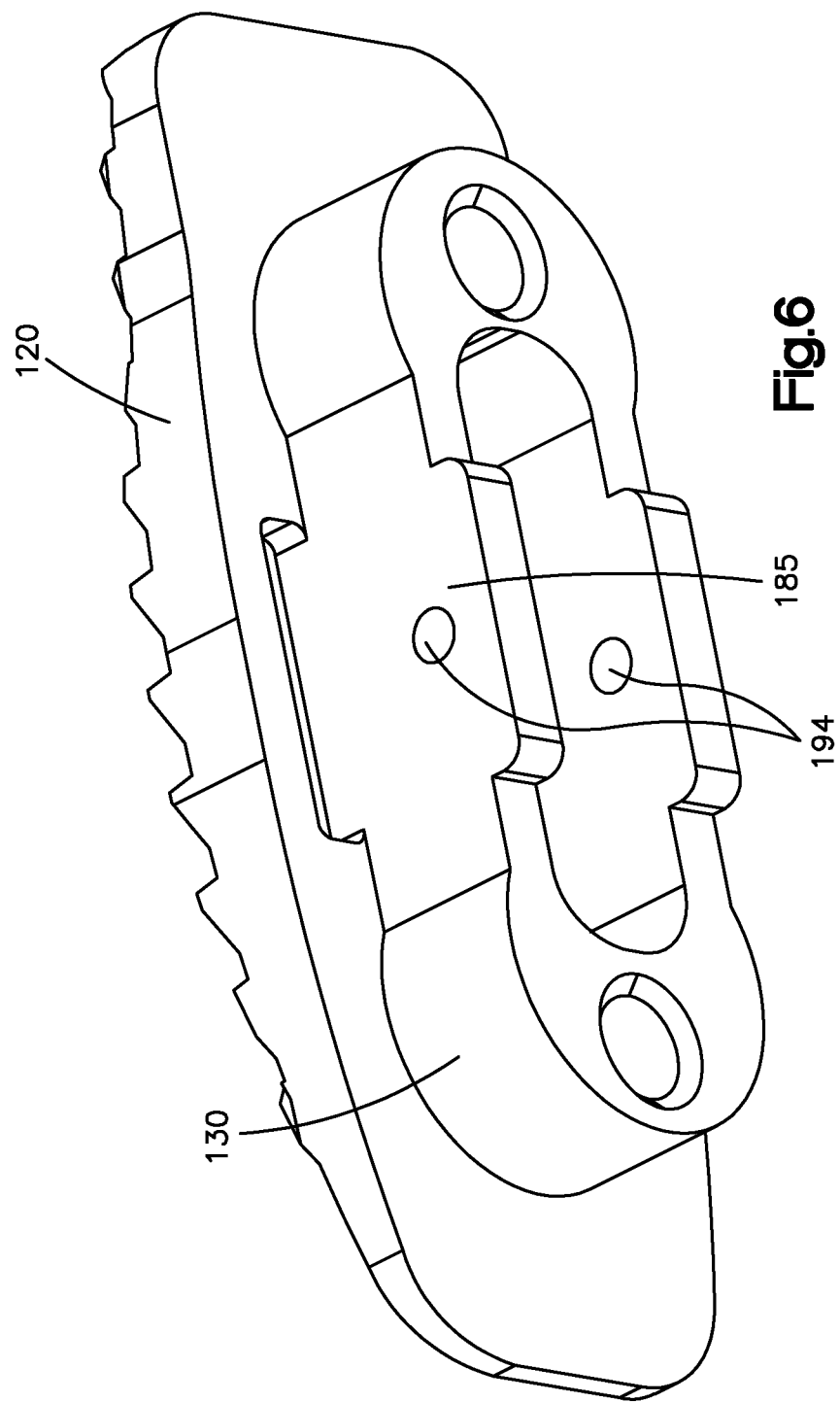
FIG. 6 illustrates a bottom perspective view of a superior component of the expandable interbody spacer shown in FIG. 4.

Referring to FIGS. 4-6, a second embodiment of an expandable interbody spacer 110 includes two separate inwardly-facing single stacks 192, 194 of C-shaped clips 170 and at least one axial bore 123 formed in its endplates 122, 142 for graft packing. The axial bore 123 extends through the interbody spacer 110 due in part to the separation of the clips 170 into two single and separate stacks 192, 194 and the removal of the central connecting portions 72 of the first embodiment. The clips 170 that are included in the expandable interbody spacer of the second embodiment are slightly less round and the resilient arms 174, 176 have a generally V-shape. There are three clips 170a, 170b, 170c in each of the stacks 192, 194 in the embodiment of FIGS. 4-6. The clips in each stack 192, 194 are integral and comprise a connecting portion 172 and resilient, flexible arms 174, 176 extending from the connecting portion 172. The two clip stacks 192, 194 are positioned so the arms at least partially surround the post members 150 and the post members 170 pass through the space 175 defined by the arms 174, 176. The stack of clips 192, 194 preferably are secured to the anterior component 140. The separate stacks 192, 194 are positioned between the outer perimeter edge of the end plate 122, 142 and the post members 150.

The superior component 120 as shown in FIG. 6 has a single unitary boss member 130. The space 175 defined by the arms 174, 176 of the clips 170 in the non-radially expanded condition, or relaxed position, is too small to permit the boss member 130 to pass through, and the arms 174, 176 in the relaxed position interfere with boss member 130 from moving through space 175. To assemble the implant, the clips 170, and in particularly the flexible, resilient arms 174, 176, are expanded to the expanded position to permit the boss member 130 to slide over post members 150 and through space 175. In use, as the superior component 120 moves relative to the inferior component, the boss member 130 also moves. When the distal end surface 134 of the boss member 130 moves past the top surface 173 of the clips 170, the resilient arms 174, 176 move inward underneath the boss member 130. If an axial compression force is applied to the spacer, the boss member will be supported by the clip 170 and will not collapse to its original size. The individual clips 170a, 170b, 170c of the clip stacks 192, 194 may be circularly-shaped, C-shaped, V-shaped, U-shaped, Y-shaped or nearly any shape that interacts with the boss member and preferably accommodates the axial bore 123 extending through the spacer 110.

The endplates 122, 142 of the second embodiment of the interbody spacer 110 also include a pin/slot mechanism 185 on each side of the expandable interbody spacer 110 that preferably prevents overexpansion. More specifically, the inferior component includes tabs 190, one on each side, that extend up from the inferior component toward the superior component. The tabs 190 include a slot 192. The boss member 120 includes a central section which preferably has two bores 194. When the inferior component and superior component are assembled, bore 194 aligns with slot 192 and a pin 195 is inserted through the bore 194 and slot 192. The pin 195 is permitted to slide in the slot 192 as the superior and inferior components move relative to each other until the pin 195 contacts the ends of the slot 192 and acts as a stop mechanism 185 to prevent the spacer from disassembling. The spacer may have one or more tabs with slots, and corresponding bores and pins.

Figure 7:
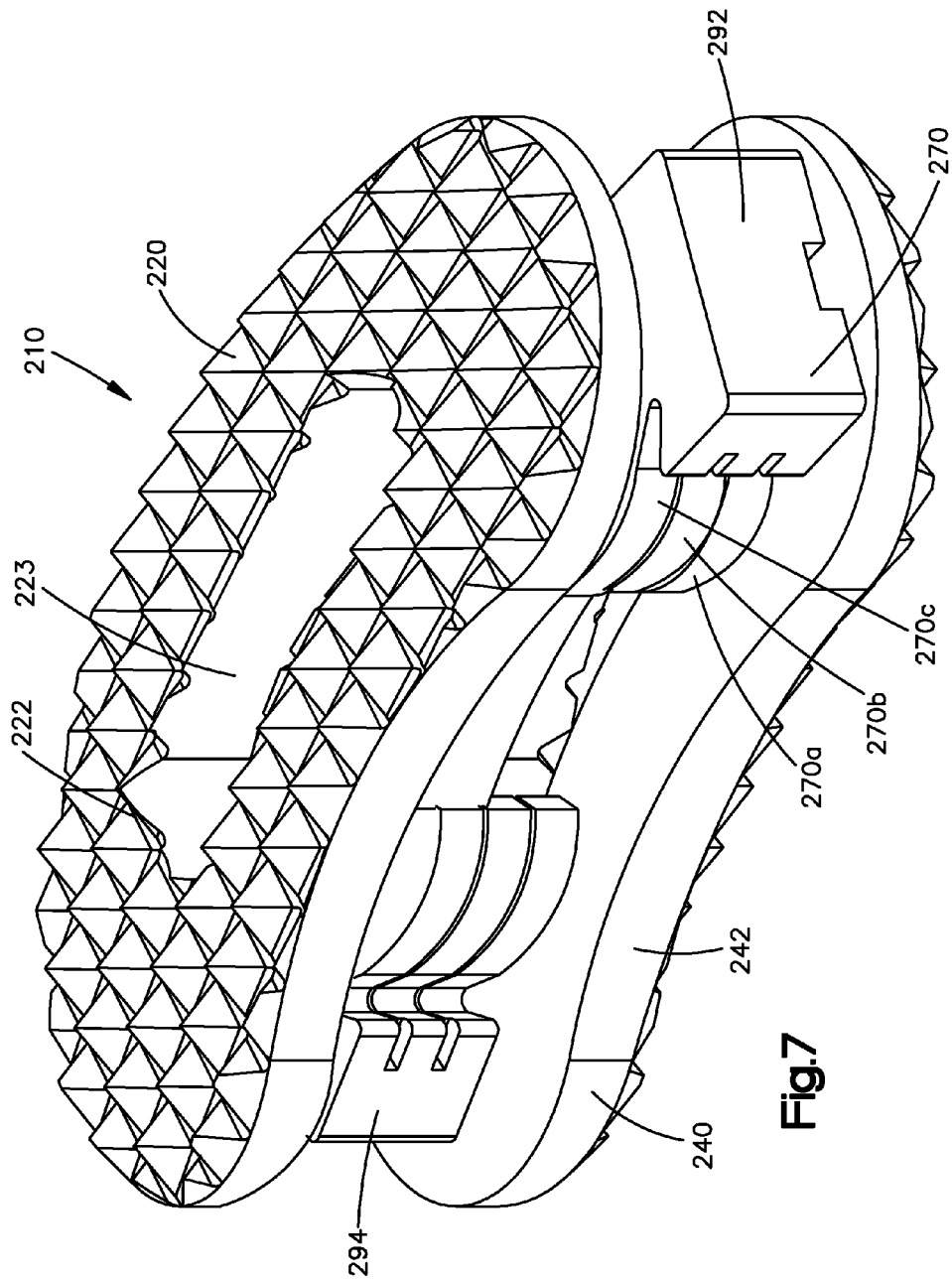
FIG. 7 illustrates a top perspective view of a third embodiment of an expandable interbody spacer in accordance with the present invention.
Figure 8:
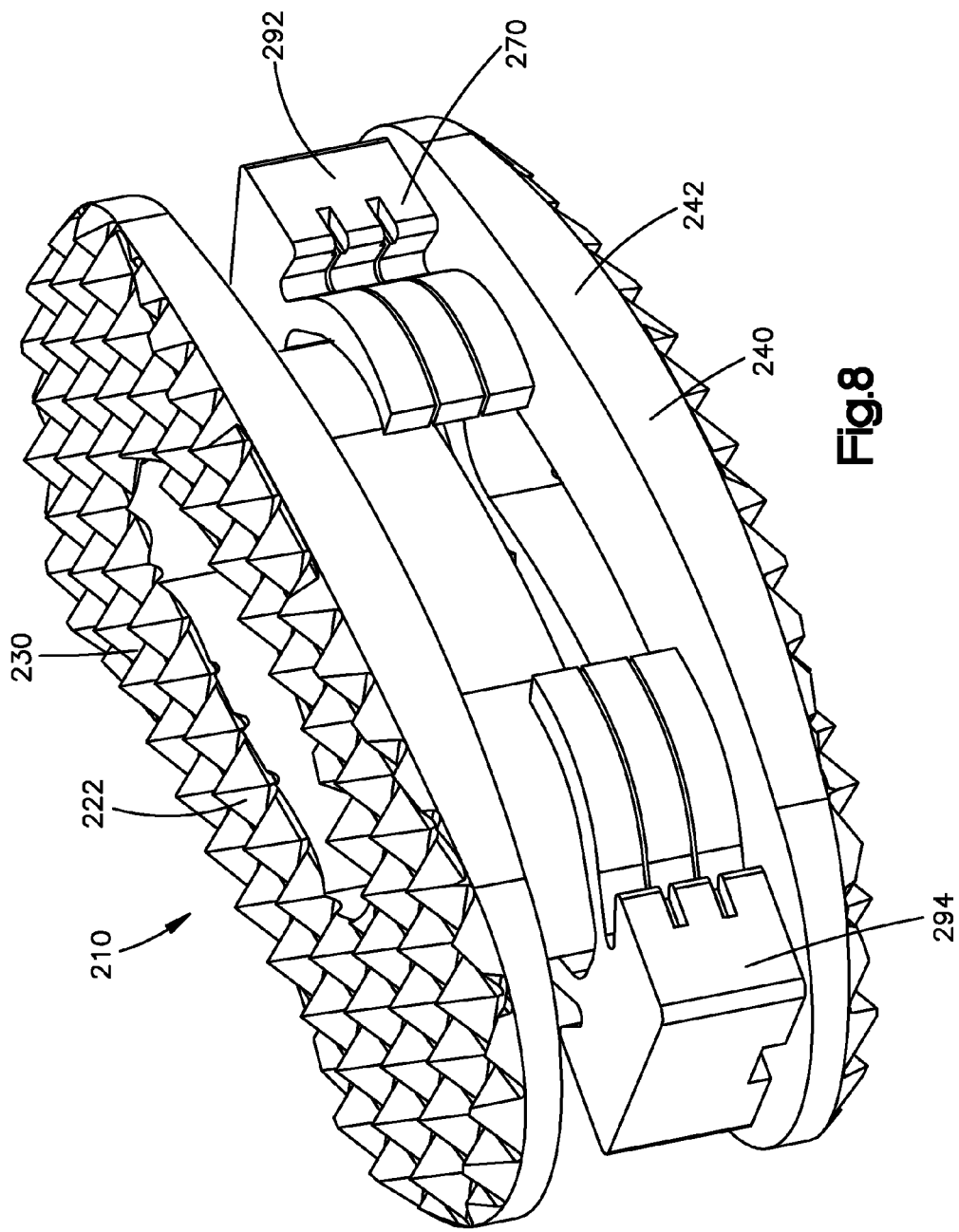
FIG. 8 illustrates a side perspective view of the expandable interbody spacer shown in FIG. 7.

The footprint of the inferior and/or superior component of the expandable interbody spacers 10, 110, 210 can be somewhat rectangular in shape, as shown in the first and second embodiments of FIGS. 1-6, or can be curved, as shown in a third embodiment of the interbody spacer 210 of FIGS. 7-8. Other shapes, configurations and sizes of the superior and inferior components, as well as shape, configuration and size of expandable spacer, are contemplated. In addition to the different shapes and sizes, the inferior and superior components of the spacers may have one or more openings that may extend partially or entirely through the spacer for receiving grafting material to assist in fusing the bone between the vertebra. Furthermore, the spacers can use many different configurations and arrangements of the clip members, bosses or boss elements, and post members.

Referring to FIGS. 9-11, an embodiment of an expandable interbody corpectomy device 310 includes a single stack 390 of clips 370, a single boss 330, and a single cylindrical protrusion 350. The expandable interbody corpectomy device 310 also includes a housing 360 (shown in phantom in FIG. 9) that generally covers the moving parts of the device 310 in the collapsed position and includes a window 365 (FIG. 10) to provide access for actuation of the device 310.

The corpectomy device has a superior component 320 and an inferior component 340. The inferior component may comprise a portion of the housing 360 and/or the protrusion 350. The protrusion 350 may be separate from or integral with the inferior component 340, and may or may not be secured to the inferior component 340. The housing 360, protrusion 350 and inferior component 340 may be an integral piece or all separate pieces, or a combination of integral pieces and separate pieces. The end faces or end plates 322, 342 of the superior and inferior components may be smooth as illustrated or may include a series of teeth, ridges, spikes, keels or surface texturing to assist with securing the corpectomy device 310 in position between vertebrae.

The corpectomy device 310 may be cylindrically shaped with circularly shaped end faces 322, 342 as shown, or the corpectomy device 310 and end faces 322, 342 may take any desirable shape, such as, for example, those illustrated in FIGS. 1-8, or other shapes. The end plates 322, 342 may also have openings 323, 343 (not shown), and the corpectomy device 310 may have a generally hollow interior in order to pack the corpectomy device 310 with bone grafting material during a procedure to assist in bone formation. The window 365 may communicate with the hollow interior of the implant and the openings 323, 343 to assist in packing the implant, spacer or corpectomy cage with bone grafting material.

Figure 13:
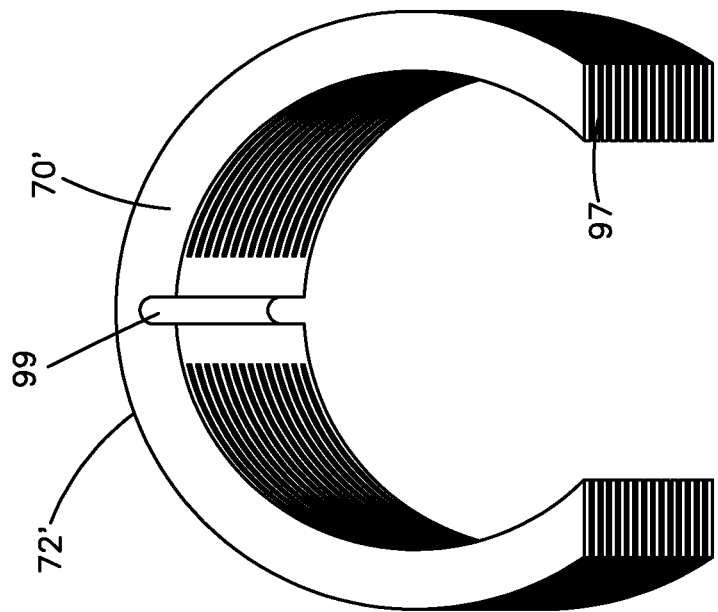
FIG. 13 illustrates a top perspective view of the stack of clip members shown in FIG. 12.
Figure 12:
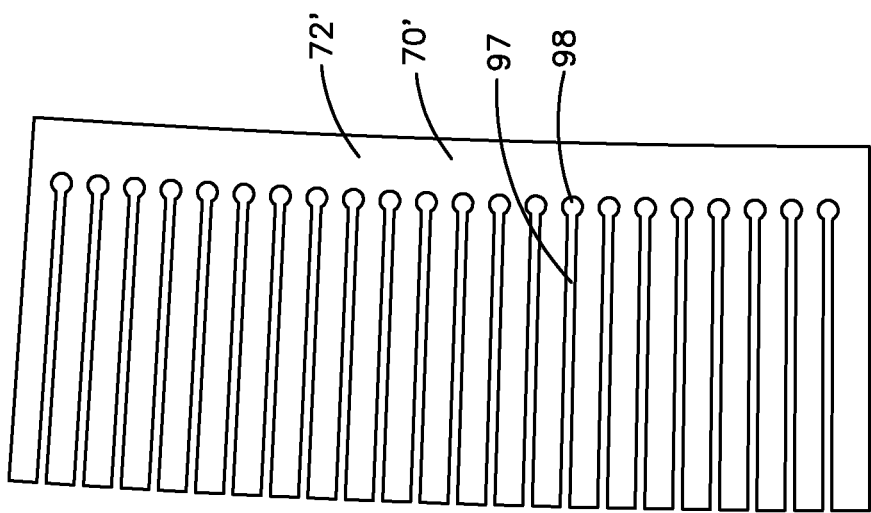
FIG. 12 illustrates a side elevational view of a stack of clip members for use in the expandable corpectomy device shown in FIG. 9.
Figure 14:
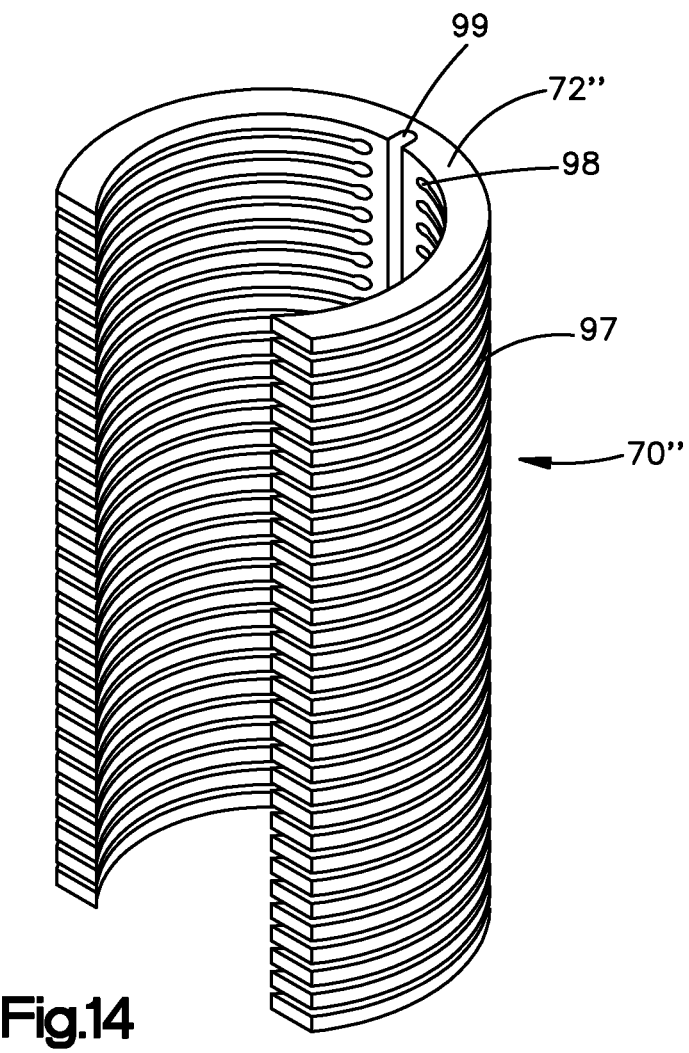
FIG. 14 illustrates a front perspective view of the stack of clip members shown in FIG. 12.

The protrusion 350 and boss 330 are both shown as cylindrically shaped in FIGS. 9-11, but may have any desirable shape including, but not limited to, the shapes and configurations shown in FIGS. 12-14. The clip stack 390 in the embodiment of FIGS. 9-11 has five clips, 370a, 370b, 370c, 370c, and 370e but may have more or less clips depending upon the results desired. The clips 370 may be integral by a connecting member or separate clips. The clips in the embodiment of FIGS. 9-11 is circularly shaped with a slot, like an O-ring, but may also be any shaped desired.

The corpectomy device 310 works in a manner similar to the embodiments of FIGS. 1-8. In the fully expanded condition the distal end of the boss 330 is positioned on top of the top surface of clip 370e. Any force or axial compression transmitted from a vertebrae to the superior surface 322 of the corpectomy device is transmitted to the boss 330. The boss 330 transmits the force to the stack 390 of clips 370 which transmits the force to the inferior component of the corpectomy device and to the inferior vertebrae. The corpectomy device would be implanted preferably in its collapsed state. In the collapsed state, the protrusion 350 is inserted into the hollow space or recess of the boss 330, and the clips 370 at least partially surround the exterior side surface of the boss 330. The clips 370 surrounding the boss are preferably in their expanded state where the arms of the clip are expanded or flexed outward to permit the boss to be inserted into the space defined by the arms of the clip.

As the corpectomy device is expanded the boss 330 moves relative to the clips 370. As the distal end 334 of the boss 330 moves past the top surface 371a of the first clip 370a, the first clip 370a returns to its relaxed position wherein the arms 374a, 376a of the clip 370a return to their non-expanded, non-flexed position (relaxed position) and move underneath the boss 330. The boss 330 is then supported by the first clip 370a and the corpectomy device 310 will retain the new height which has been increased by the thickness of the clip 370a. If further height adjustment is desired the endplates are expanded which moves the boss 330 relative to the clips 370 until the distal end surface 334 of the boss 330 moves past the top surface 371b of clip 370b where upon the second clip 370b returns to its relaxed position and the arms of the clip 370b move underneath the boss so that the clip 370b can support a load applied to the boss. The expansion of the implant may continue until a desired height is reached and in this manner the corpectomy device 310, like the vertebral spacers 10, 110, 210, are step-wise incrementally adjustable to different sizes in predefined increments.

Further illustrations of expandable corpectomy devices and design components are shown in FIGS. 12-14. Specifically, FIGS. 12-14 disclose the clip stack 70' having an integral spine 72' that joins the individual clips. The clip stack 70' may be formed of a single piece of material where slots or grooves 97 are formed in the material to form the separate clips which remain integrally connected. The grooves may also include relief radius sections 98 at the end of the groove 97. The stack 70' may further include a recess 99 to assist with the flexibility of the clips.

Figure 15:
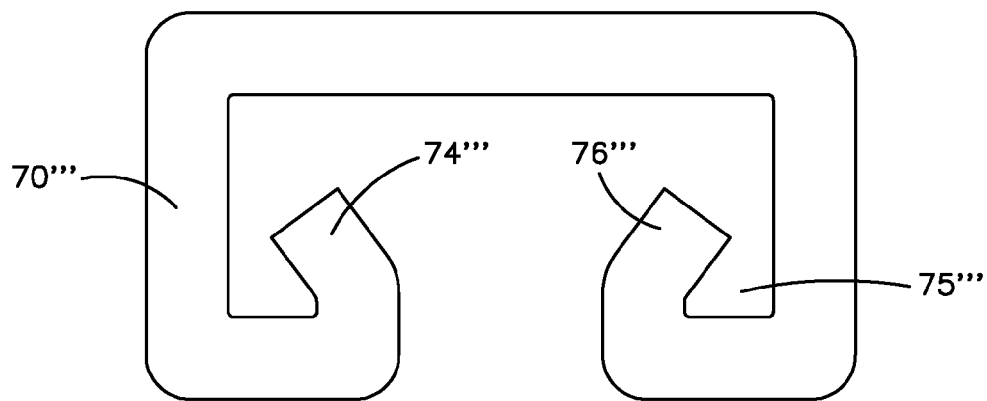
FIG. 15 illustrates a top plan view of an alternative embodiment of a stack of clip members.
Figure 16:
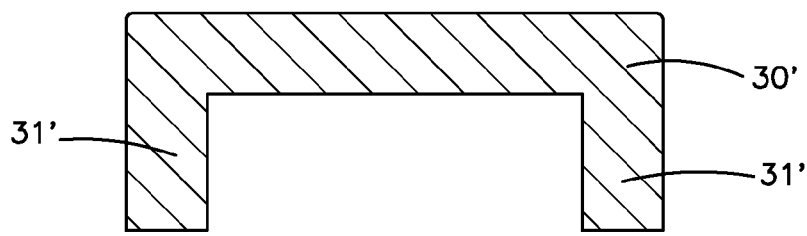
FIG. 16 illustrates a cross sectional end view of an alternative embodiment of a boss member for use with the expandable interbody spacer of FIG. 1.
Figure 17:
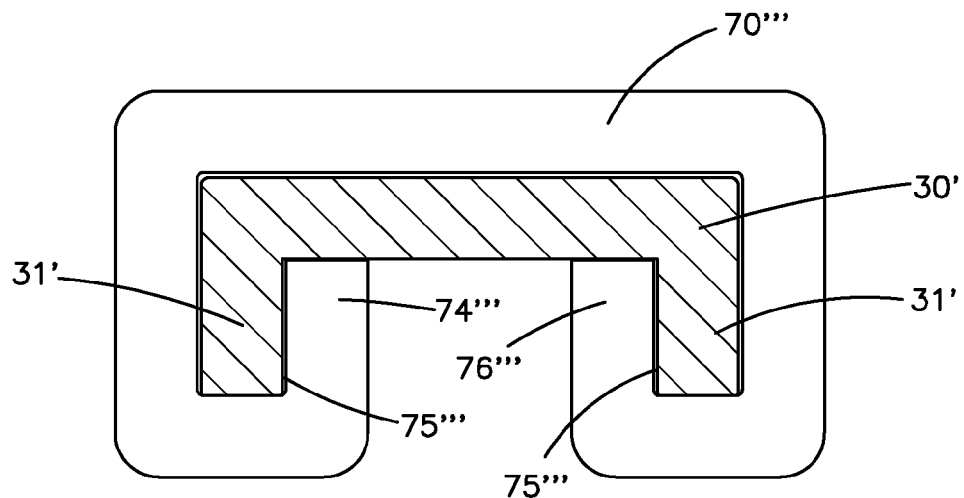
FIG. 17 illustrates the stacked clip members of FIG. 15 interacting with the boss member of FIG. 16.

The clips may take other shapes and configurations other than illustrated in FIGS. 1-14. For example, the clips may take the shape shown in FIG. 15 which is basically an open ended rectangular or U-shape where arms 74''', 76''' can expand or flex between the relaxed position in FIG. 15 and the expanded position shown in FIG. 18. The boss 30' as shown in FIGS. 16 and 17 would also be an open ended rectangular shape or U-shape where extensions 31' would fit within the space 75''' formed by the arms 74''', 76''', when the arms are in the expanded position.

Figure 18:
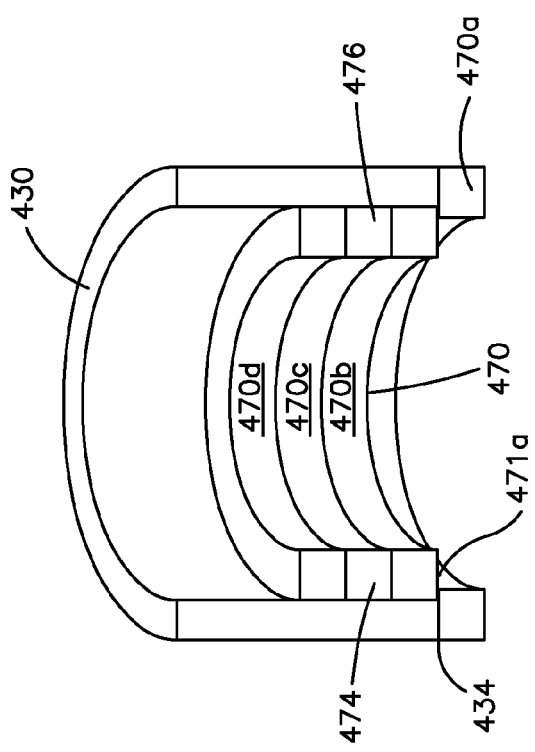
FIG. 18 illustrates an alternative embodiment of a stack of clip members and a boss member.

As shown in FIG. 18, the boss member 430 in the implant, spacer or corpectomy device may be configured so that it at least partially surrounds the clip members 470 or clip stack 490 when the implant, spacer or corpectomy device is in the collapsed or non-fully-expanded position. The clips 470 in FIG. 18 in their relaxed condition or state are sized to interfere with movement of the boss member. That is in the relaxed condition the boss 430 can not fit over or around the clip members. In the embodiment of FIG. 18, the clips 470b, 470c, 470d are contracted so that the arms 474, 476 of the clip are closer together to permit the boss 430 to move over and partially surround or overlap the clip member. As the boss member 430 moves relative to the clip member and the end surface 434 of the boss member 430 moves past the end surface 471a of the clip member 470a, the arms 474a, 476a of the clip member expand to a position underneath of and in support of the boss 430. The implant, spacer or corpectomy device may be configured in either manner so that the clip members may be expanded or alternatively contracted so that the clip members do not interfere or block movement of the boss member.

While the boss members, the post elements and protrusions, clip members and clip stacks have been shown as generally straight and which permit straight axial movement, the boss members, post or protrusion members, clip members and/or the clip stacks may be curved so that the implant, spacer or corpectomy device endplates or faces can be angled with respect to each other. Alternatively or additionally, the clip members may have non-uniform thickness or curves so that the endplates of the implant may be angled with respect to each other. These features may assist in restoring proper alignment of the vertebrae and may restore a lordotic curve or a kyphotic curve.

Figure 19:
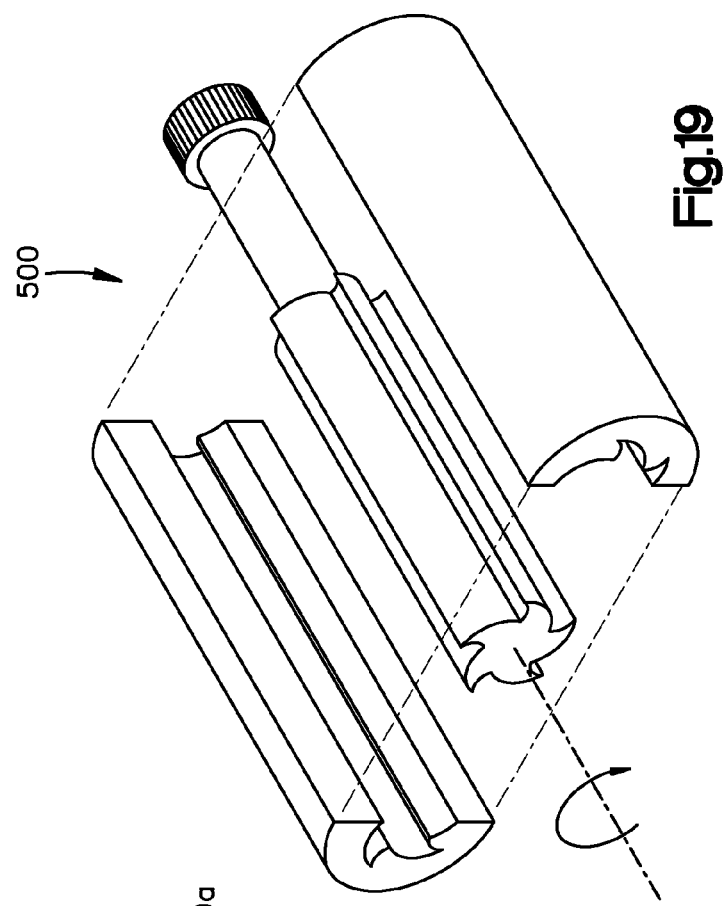
FIG. 19 illustrates a top perspective, partially exploded view of a mechanical ratcheting, expandable interbody spacer or expandable corpectomy device in accordance with another embodiment of the present invention.

FIG. 19 illustrates an embodiment of a radially, mechanical ratcheting, expandable interbody spacer or expandable corpectomy device 500.

Figure 20:
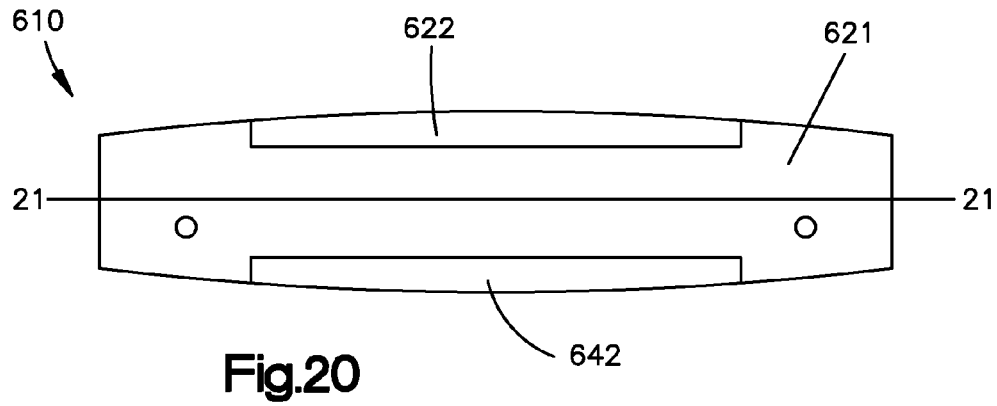
FIG. 20 illustrates a side elevational view of a mechanically expandable interbody spacer in accordance with another embodiment of the present invention.
Figure 21:
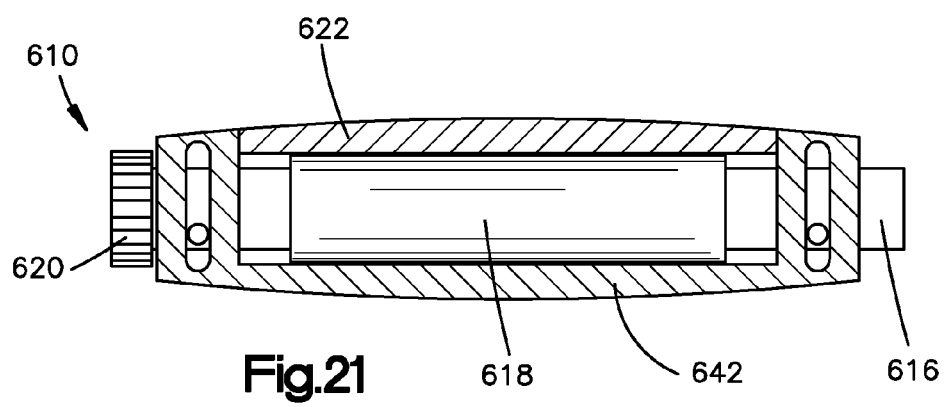
FIG. 21 illustrates a cross-sectional view of the expandable interbody spacer of FIG. 20 in a collapsed position, taken along line 21-21 of FIG. 20.
Figure 22:
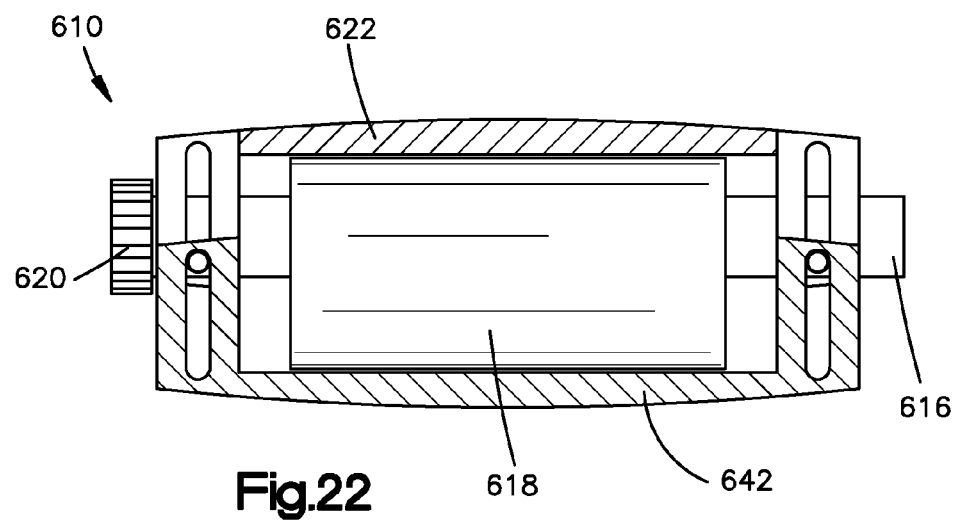
FIG. 22 illustrates a cross-sectional view of the expandable interbody spacer of FIG. 20 in an expanded position, taken along line 21-21 of FIG. 20.

FIGS. 20-22 illustrates an embodiment of a mechanical, expandable interbody spacer device 510 that includes oppositely facing upper and lower endplates 622, 642 disposed around a shaft 616 that preferably has an elliptical camming surface 618. The shaft 616 further includes a gear 620 on one end that can interface with a feature extending from one or both of the endplates 622, 642. Starting from a collapsed position in FIGS. 20 and 21, as the shaft 616 and gear 620 are rotated, the camming surface 618 pushes the endplates 622, 642 apart in the cranial/caudal direction, thereby moving the device 610 to an expanded position shown in FIG. 22. Once the desired height of the device 610 is obtained, the gear 620 is pushed inwardly and engages an interface feature (not shown) to lock the desired height, such as between 6 mm and 18 mm. The described height range of between 6 mm and 18 mm is not limiting and the device 610 may be expanded to a variety of different heights, depending upon the anatomy of the patient receiving the implant/device 610, preferences of the surgeon and related factors.

Figure 23:
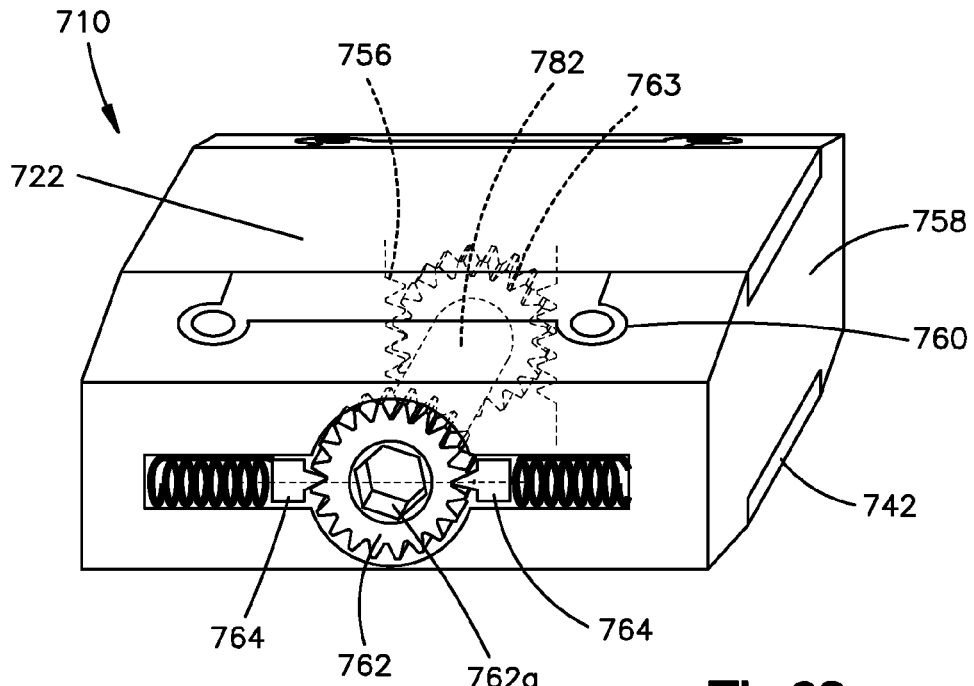
FIG. 23 illustrates a top perspective view of a mechanical ratcheting, expandable interbody spacer in accordance with yet another embodiment of the present invention shown in a collapsed position.
Figure 24:
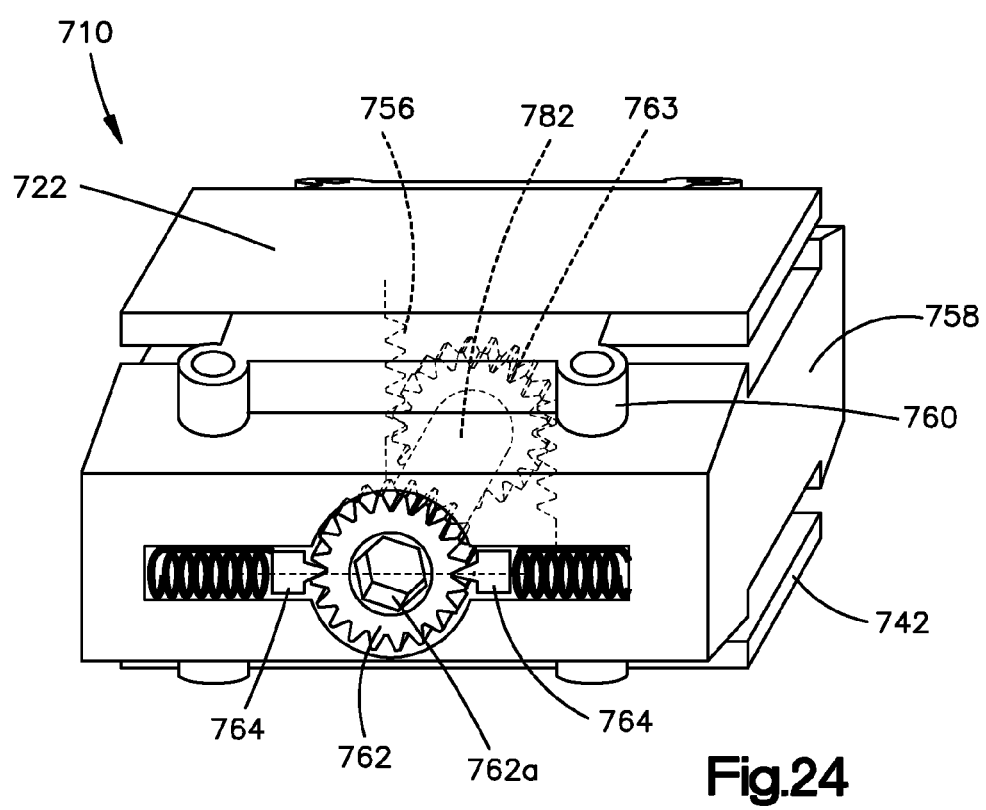
FIG. 24 illustrates a top perspective view of the expandable interbody spacer of FIG. 23, shown in an expanded position.

FIG. 23-24 illustrates another embodiment of an expandable interbody spacer 710 that includes a pair of oppositely facing endplates 722, 742, each of which further include a ridged rack 756 that runs in the cranial/caudal direction. The endplates 722, 742 are preferably disposed within a body 758 via a plurality of cylindrical bosses 760. Within the body 758 there is preferably included a shaft 782 that further includes gears 762 on either end and is disposed at the center of the expandable interbody spacer 710. Disposed on either of the gears 762 is a depression 762a that is formed to allow torque to be applied to the shaft via an instrument (not shown). In a fully collapsed condition, either gear 762 is urged to rotate as far as possible in a first direction to move the spacer 710 from a collapsed position (FIG. 23) to an expanded position (FIG. 24). A central gear 763 is disposed at the center of the expandable interbody spacer 710 and is mounted to the shaft. The central gear 763 preferably interfaces with the ridged racks 756 as a tool interfaces with and applies torque to the shaft through one or both of the gears 762. When the tool rotates the shaft 782 in a second direction, the central gear 783 causes the endplates 722, 742 to expand in the cranial/caudal direction by translating the ridged gear. Once a desired height is obtained, one of the gears 762 preferably engages a feature on the implant body 758 to lock the shaft from further rotation. For example, spring loaded stops 764 may be mounted to the body 758 to lock the shaft 782 and gears 762 in position to set the desired height.

Figure 25:
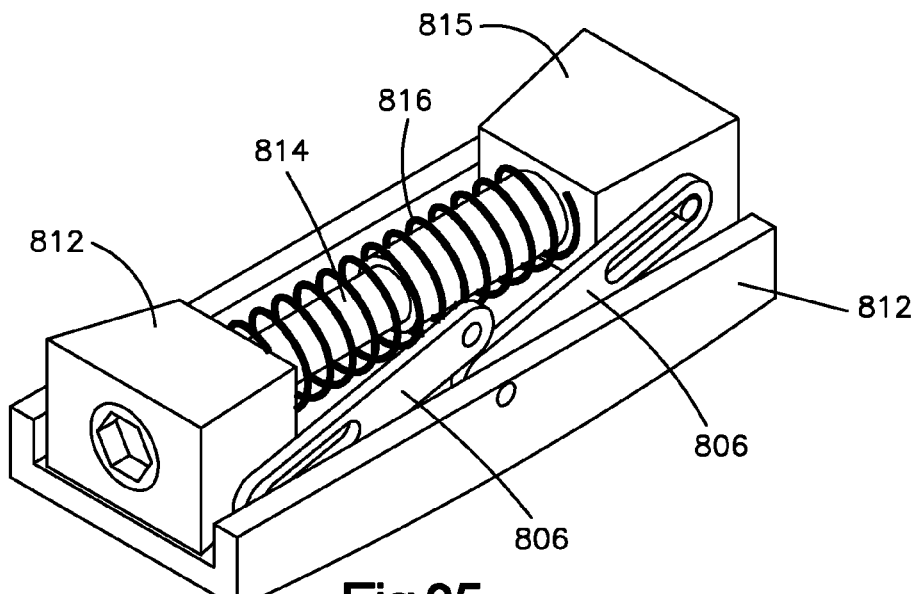
FIG. 25 illustrates a top perspective view of a mechanically expandable interbody spacer in accordance with another embodiment of the present invention, wherein a superior component is removed for clarity.
Figure 26:
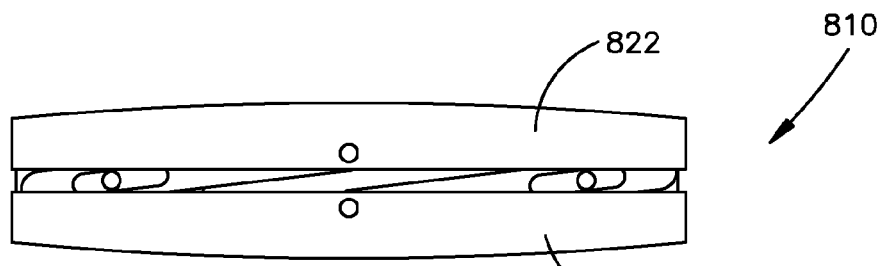
FIG. 26 illustrates a side elevational view of the expandable spacer of FIG. 25, shown in a collapsed position.
Figure 27:
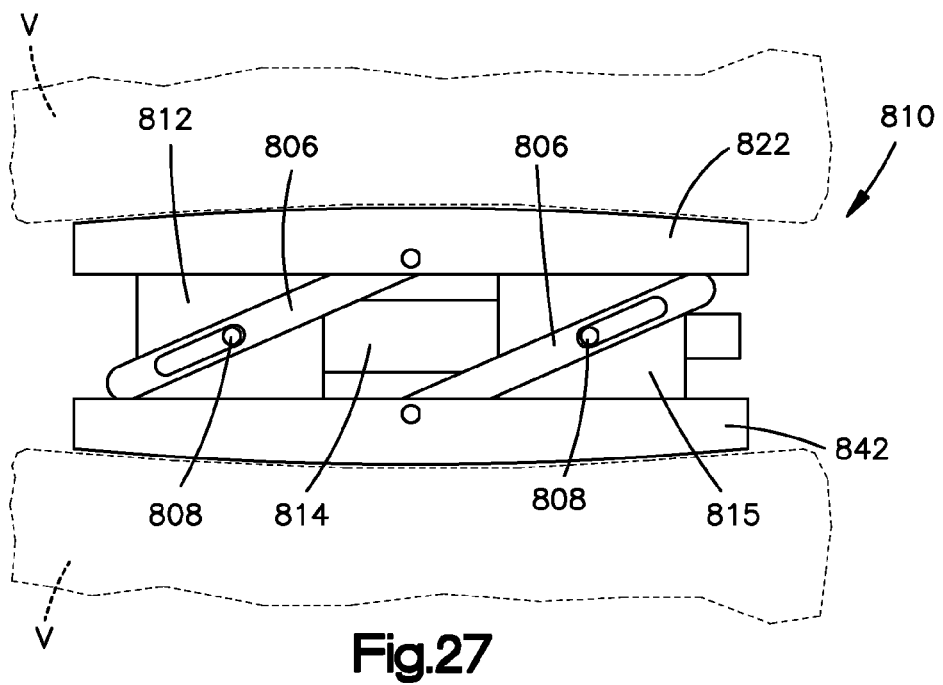
FIG. 27 illustrates a side elevational view of the expandable spacer of FIG. 25, shown in an expanded position.

FIGS. 25-27 illustrate a further embodiment of a mechanical, expandable interbody spacer 810 that includes a pair of oppositely facing endplate components 822, 842, each of which are attached to a link 806 on either side of the expandable interbody spacer 810 with a pin 808. The expandable interbody spacer 810 further includes two blocks 812, 815 disposed between the endplates 822, 842, preferably at opposite ends from one another. The blocks 812, 815 are preferably connected to one another by a screw 814, but are not so limited and may be connected to each other with nearly any mechanism that permits urging of the blocks 812, 815 toward and/or away from each other, as will be described further below. A spring 816 preferably surrounds the shaft of the screw 814 between the two blocks 812, 815. In a fully collapsed position (FIG. 26), the blocks 812, 815 are positioned in relatively close proximity to each other. A tool engages the screw 814 and is used to turn the screw 814 at the posterior end of the expandable interbody spacer 810. As the screw 814 is rotated the blocks 812, 815 move toward each other, thereby forcing the links 806 to orient themselves more vertically and the endplates 822, 842 to move away from each other. As the links 806 shift, they push the endplates 822, 842 in the cranial/caudal direction.

It will be appreciated by those skilled in the art that changes could be made to the embodiments described above without departing from the broad inventive concept thereof. For example, the features and configurations can be applied singularly or in combination and the boss elements, clip members may take on an number of different shapes and configurations, and the implant, spacer or corpectomy device may optionally include post members, or optionally stop mechanisms to prevent disassembly. While the embodiments disclosed have been referred to as spacers or corpectomy devices, the present invention is not so limited to such implant devices and may be referred to by different terms, and may be used in other parts of the body besides the spine and in non-medical applications. It is understood, therefore, that this invention is not limited to the particular embodiments disclosed, but it is intended to cover modifications within the spirit and scope of the present invention as defined by the appended claims.

We claim:

1. An expandable interbody spacer for implantation between vertebra having a collapsed condition and an expanded condition, the spacer comprising:
   a superior component having an external surface for contacting at least a portion of one vertebrae;
   an inferior component having an external surface for contacting at least a portion of another vertebrae, the superior and inferior components moveable relative to each other so that the spacer may move between the collapsed condition and the expanded condition;
   at least one boss member positioned between and moveable relative to at least one of the superior component and interior component, the boss member including a side surface and a distal end surface; and
   at least one expandable clip member, each clip member having a top surface, a relaxed position, a deflected position, and a space, wherein the boss member is arranged and configured to pass through the space when the clip member is in the deflected position and the clip member interferes with the movement of and does not permit the boss member to pass through the space when the clip member is in the relaxed position, each of the clip members being in the deflected position when the spacer is in the collapsed position, each of the clip members deflecting in a series to the relaxed position as the distal end surface of the boss member passes a top surface of each of the clips as the spacer expands thereby allowing the spacer to expand in predefined increments.

2. The spacer of claim 1 comprising a plurality of clip members, each clip member stacked one on top of the other to form at least one stack of clip members.

3. The spacer of claim 2 comprising more than one stack of clip members, each stack comprising a plurality of clip members.

4. The spacer of claim 1 wherein the clip members have integral resilient and elastically deflectable arms that move upon application of a force.

5. The spacer of claim 4 wherein the clip members are formed of a single piece of material and integrally connected.

6. The spacer of claim 1 wherein the clip members are relatively flat and have a relatively uniform thickness.

7. The spacer of claim 1 wherein the clip members are wedge shaped.

8. The spacer of claim 1 wherein the superior component includes at least one boss member extending from the superior component toward the inferior component, and the inferior component includes a post member extending from the inferior component toward the superior component, wherein the post member is associated with the boss member such that the post member may telescope with respect to the boss member as the implant expands and collapses.

9. The spacer of claim 8 wherein the clip members are secured to the inferior component.

10. The spacer of claim 1 further comprising a plurality of boss members, a plurality of post members, a plurality of clip members forming a plurality of stacks of clip members.

11. The spacer of claim 10 wherein the plurality of stacks of clip members are connected by a central member located between the plurality of boss members.

12. The spacer of claim 10 wherein the boss members and the post members are cylindrically shaped.

13. The spacer of claim 10, wherein the boss member has a recess and the post member moves within the recess as the implant moves between the collapsed and expanded conditions.

14. The spacer of claim 10 wherein the clip members have resilient arms that expand upon application of a force.

15. The spacer of claim 14 wherein the arms of the clip members are at least one of the group of circularly shaped, C-shaped, U-shaped, Y-shaped, and V-shaped.

16. The spacer of claim 14 wherein the plurality of stacked clips form at least two separate stacks of clip members, each stack of clip members associated with a different boss member.

17. The spacer of claim 16 wherein the superior and inferior components include edges along their perimeter, the separately stacked clip members located between the boss members and perimeter edges of the superior and inferior components.

18. The spacer of claim 1 wherein the clip members move to a relaxed position underneath the boss member as the distal end of the boss member passes the top surface of the clip member and supports the superior component when subjected to axial compression.

19. The spacer of claim 1 wherein the clip members have arms that are expanded and move away from each other when the clip member is changed to the deflected position such that the space defined by the clip member is larger.

20. The spacer of claim 1 wherein the clip members have arms that deflect inwardly when the clip members are changed to the deflected position.

21. The spacer of claim 1 further comprising a stop mechanism to limit the expansion of the spacer.

* * * * *